US006610474B1

(12) United States Patent
Huang

(10) Patent No.: US 6,610,474 B1
(45) Date of Patent: Aug. 26, 2003

(54) CELLS FOR DETECTION OF INFLUENZA AND PARAINFLUENZA VIRUSES

(75) Inventor: Yung T. Huang, Richmond Heights, OH (US)

(73) Assignee: University Hospitals of Cleveland, Cleveland, OH (US)

( * ) Notice: Subject to any disclaimer, the term of this patent is extended or adjusted under 35 U.S.C. 154(b) by 0 days.

(21) Appl. No.: 10/133,910

(22) Filed: Apr. 25, 2002

(51) Int. Cl.$^7$ .......................... C12Q 1/70; C12Q 1/04; C12N 5/10; C12N 7/00; C12N 7/02
(52) U.S. Cl. ..................... 435/5; 435/34; 435/235.1; 435/239; 435/325; 435/347; 435/975
(58) Field of Search ................. 435/325, 347, 435/5, 34, 975, 235.1, 239

(56) References Cited

U.S. PATENT DOCUMENTS

| | | | |
|---|---|---|---|
| 5,939,253 A | | 8/1999 | Scholl et al. |
| 6,168,915 B1 | | 1/2001 | Scholl et al. |
| 2002/0082224 A1 | * | 6/2002 | Jolly et al. ................. 514/44 |

OTHER PUBLICATIONS

Dubois et al (Journal of Biological Chemistry 270(5): 10618–10624, 1995).*
Schultz–Cherry et al (Journal of Clinical Microbiology 36(12): 3718–3720, 1998).*
Huang et al (Journal of Clinical Microbiology 86(1): 422–423, 2000).*
Huang and Turchek (2000) "Mink Lung Cells and Mixed Mink Lung and A549 Cells for Rapid Detection of Influenza Virus and Other Respiratory Viruses," J. Cin. Microbiol. 38:422–423.
Schultz–Cherry et al. (1998) "Mink Lung Epithelial Cells: Unique Cell Lines that Supports Influenza A and B Virus Replication," J. Clin. Microbiol. 36:3718–3720.
Steineke–Grober et al. (1992) "Influenza virus hemagglutinin with multibasic cleavage site is activated by furin, a subtilisin–like endoprotease," EMBO J. 11:2407–2414.
Walker et al. (1994) "Sequence Specificity of Furin, a Proprotein–Processing Endoprotease, for the Hemagglutinin of a Virulent Avian Influenza Virus," J. Virol. 68:1213–1218.
Morikawa et al. (1993) "Legitimate and Illegitimate Cleavage of Human Immunodeficiency Virus glycoproteins by Furin," J. Virol. 67:3601–3604.
Hallenberger et al. (1992) "Inhibition of furin–mediated cleavage activation of HIV–1 glycoprotein gp160," Nature 360:358–361.
Watanbe et al. (1995) "Engineered Serine Protease Inhibitor Prevents Furin–Catalyzed Activation of the Fusion Glycoprotein and Production of Infectious Measles Virus," J. Virol. 69:3206–3210.
Volchkov et al. (1998) "Processing of the Ebola virus glycoprotein by the proprotein convertase furin," Proc. Natl. Acad. Sci. USA 95:5762–5767.
Ortmann et al. (1994) "Proteolytic Cleavage of Wild Type and Mutants of the F Protein of Human Parainfluenza Virus type 3 by Two Subtilisin–Like Endoproteases, Furin and Kex2," J. Virol. 68:2772–2776.
van de Ven et al. (1990) "Furin is a subtilisin–like proprotein processing enzyme in higher eukaryotes," Mol. Biol. Rep. 14:265–75.
Kniazeff et al. (1976) "Characteristics of Epithelial Cells Cultured from Feline Lung," Lab. Invest. 5:495–500.
Milo et al. (1984) "Growth Characteristics, Morphology, and Phospholipid Composition of Human Type II Pulmonary Alveolar Cells Grown in a Collagen–Free Microenvironment," In Vitro, 20:899–911.
Richards et al. (1987) "Isolation, Biochemical Characterization, and Culture of Lung Type II Cells of the Rat," Lung 165:143–158.
Robinson et al. (1984) "Isolation and Culture of Human Alveolar Type II Epithelial Cells," Am. Rev. Respir. Disease 130:1156–1160.
Palache et al. (1997) "Immunogenicity and Reactogenicity of Influenza Subunit Vaccines Produced in MDCK Cells or Fertilized Chicken Eggs," J. Infect. Dis. 176(suppl. 1):S20–S23.
GenBank Accession Number X17094.
GenBank Accession Number AI344029.
Subbarao et al. (1998) "Characterization of an Avian Influenza A (H5N1) Virus Isolated from a Child with a Fatal Respiratory Illness," Science 279:393–396.
Huang et al. (2002) "Engineered BGMK Cells for Sensitive and Rapid Detection of Enteroviruses," J. Clin. Microbiol. 40:366–371.
Hosaka et al. (1991) "Arg–X–Lys/Arg–Arg Motif as a Signal for Precursor Cleavage Catalyzed by Furin within the Constitutive Secretory Pathway," J. Biol. Chem. 266:12127–12130.
Klimstra et al. (1999) "The Furin Protease Cleavage Recognition Sequence of Sindbis Virus PE2 Can Mediate Virior Attachment to Cell Surface Heparan Sulfate," J. Virology 73:6299–6306.
Moehring et al. (1993) "Expression of Mouse Furin in a Chinese Hamster Cell Resistant to Pseudomonas Exotoxin A and Viruses Complements the Genetic Lesion," J. Biol. Chem. 268:2590–2594.

(List continued on next page.)

Primary Examiner—Mary E. Mosher
(74) Attorney, Agent, or Firm—Medlen & Carroll LLP

(57) ABSTRACT

The invention provides cell lines which are useful for the rapid detection and production of influenza and parainfluenza viruses. In particular, the invention relates to transgenic mink lung cells which show increased sensitivity to infection by influenza A, influenza B, or parainfluenza 3 viruses, or which are capable of enhanced productivity of infectious virions. The invention is suitable for use in culturing clinical influenza and parainfluenza virus isolates and for the production of influenza and parainfluenza virus for vaccine formulations, as antigen preparations for diagnostic applications, and for screening antiviral drugs.

18 Claims, 4 Drawing Sheets

OTHER PUBLICATIONS

Ohnishi et al. (1994) "A Furin–Defective Cell Line Is Able to Process Correctly the gp160 of Human Immunodeficiency Virus Type 1," J. Virol. 68:4075–4079.

Richt et al. (1998) "Processing of the Borna Disease Virus Glycoprotein gp94 by the Subtilisin–Like Endoprotease Furin," J. Virol. 72:4528–4533.

Shapiro et al. (1997) "Localization of Endogenous Furin in Cultured Cell Lines," J. Histochem. & Cytochem. 45:3–12.

Simmen et al. (1999) "Basolateral Sorting of Furin in MDCK Cells Requires a Phenylalanine–Isoleucine Motif Together with an Acidic Amino Acid Cluster," Mol. & Cell. Biol. 19:3136–3144.

Stadler et al. (1997) "Proteolytic Activation of Tick–Borne Encephalitis Virus by Furin," J. Virol. 71:8475–8481.

* cited by examiner

```
                                        atgg agctgaggcc ctggttgcta
tgggtggtag cagcaacagg aaccttggtc ctgctagcag ctgatgctca gggccagaag
gtcttcacca acacgtgggc tgtgcgcatc cctggaggcc cagcggtggc aacagtgtg
gcacggaagc atgggttcct caacctgggc cagatcttcg gggactatta ccacttctgg
catcgaggag tgacgaagcg gtccctgtcg cctcaccgcc cgcggcacag ccggctgcag
agggagcctc aagtacagtg gctggaacag caggtggcaa agcgacggac taaacgggac
gtgtaccagg agcccacaga ccccaagttt cctcagcagt ggtacctgtc tggtgtcact
cagcgggacc tgaatgtgaa ggcggcctgg gcgcagggct acacagggca cggcattgtg
gtctccattc tggacgatgg catcgagaag aaccacccgg acttggcagg caattatgat
cctggggcca gttttgatgt caatgaccag gaccctgacc cccagcctcg gtacacacag
atgaatgaca acaggcacgg cacacggtgt gcggggaag tggctgcggt ggccaacaac
ggtgtctgtg gtgtaggtgt ggcctacaac gcccgcattg gagggtgcg catgctggat
ggcgaggtga cagatgcagt ggaggcacgc tcgctgggcc tgaaccccaa ccacatccac
atctacagtg ccagctgggg ccccgaggat gacggcaaga cagtggatgg gccagcccgc
ctcgccgagg aggccttctt ccgtggggtt agccagggcc gaggggggct gggtccccatc
tttgtctggg cctcggggaa cgggggccgg gaacatgaca gctgcaactg cgacggctac
accaacagta tctacacgct gtccatcagc agcgccacgc agtttggcaa cgtgccgtgg
tacagcgagg cctgctcgtc cacactggcc acgacctaca gcagtggcaa ccagaatgag
aagcagatcg tgacgactga cttgcggcag aagtgcacgg agtctcacac gggcacctca
gcctctgccc ccttagcagc cggcatcatt gctctcaccc tggaggcaa taagaacctc
acatggcggg acatgcaaca cctggtggta cagacctcga agccagccca cctcaatgcc
aacgactggg ccaccaatgg tgtgggccgg aaagtgagcc actcatatgg ctacgggctt
ttggacgcag gcgccatggt ggccctggcc cagaattgga ccacagtggc cccccagcgg
aagtgcatca tcgacatcct caccgagccc aaagacatcg ggaacggct cgaggtgcgg
aagaccgtga ccgcgtgcct gggcgagccc aaccacatca ctcggctgga gcacgctcag
gcgcggctca ccctgtccta taatcgccgt ggcgacctgg ccatccacct ggtcagcccc
atgggcaccc gctccaccct gctggcagcc aggccacatg actactccgc agatgggttt
aatgactggg ccttcatgac aactcattcc tgggatgagg atccctctgg cgagtgggtc
ctagagattg aaaacaccag cgaagccaac aactatggga cgctgaccaa gttcaccctc
gtactctatg gcaccgcccc tgaggggctg cccgtacctc cagaaagcag tggctgcaag
accctcacgt ccagtcaggc ctgtgtggtg tgcgaggaag gcttctccct gcaccagaag
agctgtgtcc agcactgccc tccaggcttc gccccccaag tcctcgatac gcactatagc
accgagaatg acgtggagac catccgggcc agcgtctgcg ccccctgcca cgcctcatgt
gccacatgcc aggggccggc cctgacagac tgcctcagct gccccagcca cgcctccttg
gaccctgtgg agcagacttg ctcccggcaa agcagagca gccgagagtc cccgccacag
cagcagccac ctcggctgcc cccggaggtg gaggcgggc aacggctgcg ggcaggggctg
ctgccctcac acctgcctga ggtggtggcc ggcctcagct gcgccttcat cgtgctggtc
ttcgtcactg tcttcctggt cctgcagctg cgctctggct ttagttttcg ggggtgaag
gtgtacacca tggaccgtgg cctcatctcc tacaagggc tgccccctga agcctggcag
gaggagtgcc cgtctgactc agaagaggac gagggccggg cgagaggac cgcctttatc
aaagaccaga gcgccctctg atga
```

B

```
MELRPWLLWVVAATGTLVLLAADAQGQKVFTNTWAVRIPGGPAVANSVARKHGFLNLGQIFGDYYHFWHRGVTKRSLS
PHRPRHSRLQREPQVQWLEQQVAKRRTKRDVYQEPTDPKFPQQWYLSGVTQRDLNVKAAWAQGYTGHGIVVSILDDGI
EKNHPDLAGNYDPGASFDVNDQDPDPQPRYTQMNDNRHGTRCAGEVAAVANNGVCGVGVAYNARIGGVRMLDGEVTDA
VEARSLGLNPNHIHIYSASWGPEDDGKTVDGPARLAEEAFFRGVSQGRGGLGSIFVWASGNGGREHDSCNCDGYTNSI
YTLSISSATQFGNVPWYSEACSSTLATTYSSGNQNEKQIVTTDLRQKCTESHTGTSASAPLAAGIIALTLEANKNLTW
RDMQHLVVQTSKPAHLNANDWATNGVGRKVSHSYGYGLLDAGAMVALAQNWTTVAPQRKCIIDILTEPKDIGKRLEVR
KTVTACLGEPNHITRLEHAQARLTLSYNRRGDLAIHLVSPMGTRSTLLAARPHDYSADGFNDWAFMTTHSWDEDPSGE
WVLEIENTSEANNYGTLTKFTLVLYGTAPEGLPVPPESSGCKTLTSSQACVVCEEGFSLHQKSCVQHCPPGFAPQVLD
THYSTENDVETIRASVCAPCHASCATCQGPALTDCLSCPSHASLDPVEQTCSRQSQSSRESPPQQQPPRLPPEVEAGQ
RLRAGLLPSHLPEVVAGLSCAFIVLVFVTVFLVLQLRSGFSFRGVKVYTMDRGLISYKGLPPEAWQEECPSDSEEDEG
RGERTAFIKDQSAL
```

CELLS FOR DETECTION OF INFLUENZA AND PARAINFLUENZA VIRUSES

FIELD OF THE INVENTION

The invention provides cell lines which are useful for the rapid detection and production of influenza and parainfluenza viruses. In particular, the invention relates to transgenic mink lung cells which show increased sensitivity to infection by influenza A, influenza B, or parainfluenza 3 viruses, or which are capable of enhanced productivity of infectious virions. The invention is suitable for use in culturing clinical influenza and parainfluenza virus isolates and for the production of influenza and parainfluenza virus for vaccine formulations, as antigen preparations for diagnostic applications, and for screening antiviral drugs.

BACKGROUND OF THE INVENTION

Mink lung cells and mixed mink lung cell cultures are extremely sensitive for the rapid detection of various influenza and parainfluenza viruses (See, U.S. Pat. No. 6,168,915 herein incorporated by reference in its entirety; and Huang and Turchek, J. Clin. Microbiol. 38:422–423 [2000]). Additionally, mink lung cells have also been proposed as a potential replacement for chicken embryonated eggs and/or Madin-Darby canine kidney (MDCK) cells for the production of flu vaccines (Schultz-Cherry et al., J. Clin. Microbiol. 36:3718–3720 [1998]). However, one major drawback to the use of mink lung cells for the detection and production of influenza and parainfluenza viruses is that the virions produced from mink lung cells are not very infectious. Thus, mink lung cells are expected to be less sensitive than desirable for the late detection of cultured clinical specimens, and are not expected to be capable of producing high titer virus stocks for influenza and parainfluenza vaccine formulations.

Thus, what is needed are cells with enhanced sensitivity to influenza and parainfluenza virus infection to permit rapid detection of these respiratory viruses. Additionally, there is need in the art for cultured cells capable of producing high titers of infectious influenza and parainfluenza for use in influenza and parainfluenza vaccines.

SUMMARY OF THE INVENTION

The invention provides cell lines which are useful for the rapid detection and production of influenza and parainfluenza viruses. In particular, the invention relates to transgenic mink lung cells which show increased sensitivity to infection by influenza A, influenza B, or parainfluenza 3 viruses, or which are capable of enhanced productivity of infectious virions. The invention is suitable for use in culturing clinical influenza and parainfluenza virus isolates and for the production of influenza and parainfluenza virus for vaccine formulations, as antigen preparations for diagnostic applications, and for screening antiviral drugs.

In particular, the invention provides a transgenic cell line designated Mv1Lu-hF. The invention also provides a cell line established from a transgenic cell line designated Mv1Lu-hF, wherein the established cell line has a property selected from the group consisting of (a) increased sensitivity to at least one virus selected from the group consisting of influenza A virus, influenza B virus and parainfluenza virus 3, as compared to the Mv1Lu cell line, and (b) enhanced productivity of infectious virions upon inoculation with at least one virus selected from the group one consisting of influenza A virus, influenza B virus and parainfluenza virus 3, as compared to the Mv1Lu cell line. In some embodiments, the cell line has the sensitivity of the cell line designated Mv1Lu-hF, to at least one virus selected from the group consisting of influenza A virus, influenza B virus and parainfluenza virus.

The present invention also provides a transgenic mink lung epithelial cell line expressing human furin, wherein the cell line has a property selected from the group consisting of (a) increased sensitivity to at least one virus selected from the group consisting of influenza A virus, influenza B virus and parainfluenza virus 3, as compared to Mv1Lu, and (b) enhanced productivity of infectious virions upon inoculation with at least one virus selected from the group one consisting of influenza A virus, influenza B virus and parainfluenza virus 3, as compared to Mv1Lu. In preferred embodiments, human furin is encoded by the sequence SEQ ID NO:1. In some embodiments, the transgenic mink lung epithelial cell line has the sensitivity of the cell line designated Mv1Lu-hF to at least one virus selected from the group consisting of influenza A virus, influenza B virus and parainfluenza virus 3.

Also provided by the present invention is a composition comprising a transgenic mink lung epithelial cell expressing human furin, wherein the cell has a property selected from the group consisting of (a) increased sensitivity to at least one virus selected from the group consisting of influenza A virus, influenza B virus and parainfluenza virus 3, as compared to the Mv1Lu cell line, and (b) enhanced productivity of infectious virions upon inoculation with at least one virus selected from the group one consisting of influenza A virus, influenza B virus and parainfluenza virus 3, as compared to the Mv1Lu cell line. In some embodiments, the composition further comprises a second cell type different from the transgenic mink lung epithelial cell, and wherein the transgenic mink lung epithelial cell and the second cell type are in mixed-cell type culture. In related embodiments, the second cell type is selected from the group consisting of primary monkey kidney, BS-C-1, CV-1, Vero, Vero 76, Vero C1008, Vero 76, Cos-1, Cos-7, FRhK-4, LLC-MK2 original, LLC-MK2 derivative, MDCK, RD, A549, MRC-5, KB, and CaCo-2 cells.

The present invention also provides, a composition comprising a transgenic cell designated Mv1Lu-hF. In some embodiments, the composition further comprises a second cell type different from the Mv1Lu-hF cell, and wherein the Mv1Lu-hF cell and the second cell type are in mixed-cell type culture.

Also provided by the present invention is a composition comprising a cell established from a transgenic cell line designated Mv1Lu-hF, wherein the established cell has a property selected from the group consisting of (a) increased sensitivity to at least one virus selected from the group consisting of influenza A virus, influenza B virus and parainfluenza virus 3, as compared to the Mv1Lu cell line, and (b) enhanced productivity of infectious virions upon inoculation with at least one virus selected from the group one consisting of influenza A virus, influenza B virus and parainfluenza virus 3, as compared to the Mv1Lu cell line. In some embodiments, the composition further comprises a second cell type different from the established cell, and wherein the established cell and the second cell type are in mixed-cell type culture.

The present invention also provides a method for detection of a virus selected from the group consisting of influenza A virus, influenza B virus and parainfluenza virus 3, in a sample, comprising: a) providing: a sample suspected of containing the virus; and a composition comprising a cell designated Mv1Lu-hF; b) inoculating the cell with the sample to produce an inoculated cell; and c) observing the inoculated cell for the presence of the virus. In some embodiments, the composition further comprises a second cell type different from the Mv1Lu-hF cell, and wherein the Mv1Lu-hF cell and the second cell type are in mixed-cell type culture. In preferred embodiments, the method further comprises providing a monoclonal antibody selected from the group consisting of an influenza A virus-reactive monoclonal antibody, an influenza B virus-reactive monoclonal antibody, and a parainfluenza virus 3-reactive monoclonal antibody, and wherein step c) comprises using the monoclonal antibody for observation of the virus.

Also provided by the present invention is a kit for detection of a virus selected from the group consisting of influenza A virus, influenza B virus and parainfluenza virus 3, in a sample, comprising: a) a composition comprising a cell designated Mv1Lu-hF; and b) a monoclonal antibody selected from the group consisting of an influenza A virus-reactive monoclonal antibody, an influenza B virus-reactive monoclonal antibody, and a parainfluenza virus 3-reactive monoclonal antibody. In preferred embodiments, the composition further comprises a second cell type different from the Mv1Lu-hF cell, and wherein the Mv1Lu-hF cell and the second cell type are in mixed-cell type culture. In some embodiments, the monoclonal antibody is a fluorochrome-conjugated monoclonal antibody.

The present invention also provides a method for producing virus selected from the group consisting of influenza A virus, influenza B virus and parainfluenza virus 3, comprising: a) providing: a sample containing the virus, and a composition comprising a cell designated Mv1Lu-hF; and b) inoculating the cell with the sample to produce an inoculated cell, wherein the cell produces said virus.

BRIEF DESCRIPTION OF THE DRAWINGS

FIG. 4 provides the nucleotide sequence (SEQ ID NO:1; GenBank Accession No. X17094) (A) which encodes the human furin polypeptide sequence (SEQ ID NO:2) (B).

DEFINITIONS

Figure 1:
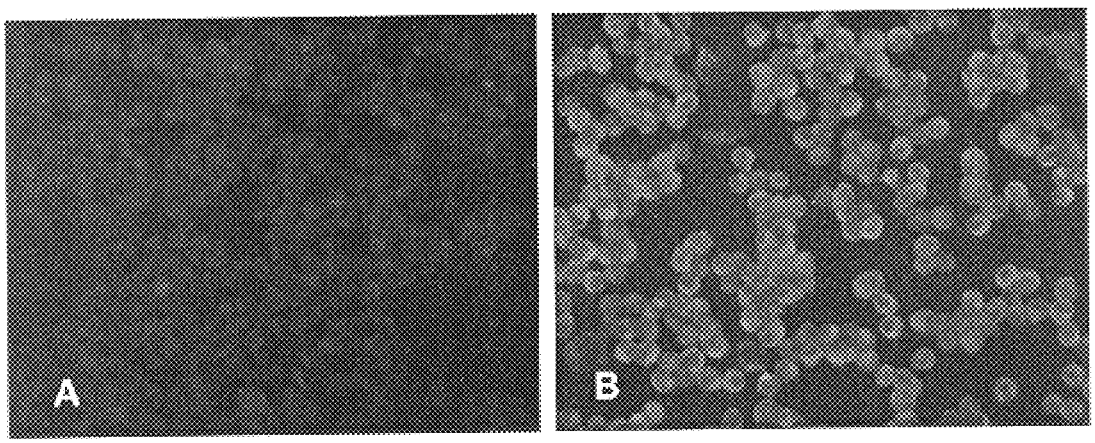
FIG. 1 shows immunofluorescence staining of human furin expressed on the surface of (A) Mv1Lu cells, and (B) transgenic Mv1Lu-hF cells.

To facilitate understanding of the invention, a number of terms are defined below.

The terms "sample" and "specimen" in the present specification and claims are used in their broadest sense to include any composition that is obtained and/or derived from biological or environmental source, as well as sampling devices (e.g., swabs) which are brought into contact with biological or environmental samples. "Biological samples" include those obtained from an animal (including humans, domestic animals, as well as feral or wild animals, such as ungulates, bear, fish, lagamorphs, rodents, etc.), body fluids such as urine, blood, fecal matter, cerebrospinal fluid (CSF), semen, sputum, and saliva, as well as solid tissue. Also included are samples obtained from food products and food ingredients such as dairy items, vegetables, meat, meat by-products, and waste. "Environmental samples" include environmental material such as surface matter, soil, water, and industrial materials, as well as material obtained from food and dairy processing instruments, apparatus, equipment, disposable, and non-disposable items. These examples are not to be construed as limiting the sample types applicable to the present invention.

As used herein, the term "cell type," refers to any cell, regardless of its source or characteristics.

As used herein, the term "microorganism" refers to any organism of microscopic or ultramicroscopic size including, but not limited to, viruses, bacteria, and protozoa.

As used herein, the term "culture" refers to a composition, whether liquid, gel, or solid, which contains one or more microorganisms and/or one or more cells. A culture of organisms and/or cells can be pure or mixed. For example, a "pure culture" of an organism as used herein refers to a culture in which the organisms present are of only one strain of a single species of a particular genus. This is in contrast to a "mixed culture" of organisms which refers to a culture in which more than one strain of a single genus and/or species of microorganism is present.

As used herein, the terms "culture media," and "cell culture media," refer to media that are suitable to support maintenance and/or growth of cells in vitro (i.e., cell cultures).

A "primary cell" is a cell which is directly obtained from a tissue or organ of an animal whether or not the cell is in culture.

A "cultured cell" is a cell which has been maintained and/or propagated in vitro. Cultured cells include primary cultured cells and cell lines.

"Primary cultured cells" are primary cells which are in in vitro culture and which preferably, though not necessarily, are capable of undergoing ten or fewer passages in in vitro culture before senescence and/or cessation of proliferation.

The terms "cell line" and "immortalized cell" refer to a cell which is capable of a greater number of cell divisions in vitro before cessation of proliferation and/or senescence as compared to a primary cell from the same source. A cell line includes, but does not require, that the cells be capable of an infinite number of cell divisions in culture. The number of cell divisions may be determined by the number of times a cell population may be passaged (i.e., subcultured) in in vitro culture. Passaging of cells is accomplished by methods known in the art. Briefly, a confluent or subconfluent population of cells which is adhered to a solid substrate (e.g., plastic Petri dish) is released from the substrate (e.g., by enzymatic digestion), and a proportion (e.g., 10%) of the released cells is seeded onto a fresh substrate. The cells are allowed to adhere to the substrate, and to proliferate in the presence of appropriate culture medium. The ability of adhered cells to proliferate may be determined visually by observing increased coverage of the solid substrate over a period of time by the adhered cells. Alternatively, proliferation of adhered cells may be determined by maintaining the initially adhered cells on the solid support over a period of time, removing and counting the adhered cells and observing an increase in the number of maintained adhered cells as compared to the number of initially adhered cells.

Cell lines may be generated spontaneously or by transfection. A "spontaneous cell line" is a cell line which arises during routine culture of cells. The terms "transfected cell line" and "transgenic cell line" refer to a cell line which is generated by the introduction of a "transgene" comprising nucleic acid (usually DNA) into a primary cell or into a cell line by way of human intervention Cell lines include, but are not limited to, finite cell lines and continuous cell lines. As used herein, the term "finite cell line" refers to a cell line which is capable of a limited number (from about 1 to about 50, more preferably from about 1 to about 40, and most preferably from about 1 to about 20) of cell divisions prior to senescence.

The term "continuous cell line" refer to a cell line which is capable of more than about 50 (and more preferably, an infinite number of) cell divisions. A continuous cell line generally, although not necessarily, also has the general characteristics of a reduced cell size, higher growth rate, higher cloning efficiency, increased tumorigenicity, and/or a variable chromosomal complement as compared to the finite cell line or primary cultured cells from which it is derived.

The term "transgene" as used herein refers to any nucleic acid sequence which is introduced into the cell by experimental manipulations. A transgene may be an "endogenous DNA sequence" or a "heterologous DNA sequence" (i.e., "foreign DNA"). The term "endogenous DNA sequence" refers to a nucleotide sequence which is naturally found in the cell into which it is introduced so long as it does not contain some modification (e.g., a point mutation, the presence of a selectable marker gene, etc.) relative to the naturally-occurring sequence. The term "heterologous DNA sequence" refers to a nucleotide sequence which is ligated to, or is manipulated to become ligated to, a nucleic acid sequence to which it is not ligated in nature, or to which it is ligated at a different location in nature. Heterologous DNA is not endogenous to the cell into which it is introduced, but has been obtained from another cell. Heterologous DNA also includes an endogenous DNA sequence which contains some modification. Generally, although not necessarily, heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc.

The term "nucleotide sequence of interest" refers to any nucleotide sequence, the manipulation of which may be deemed desirable for any reason, by one of ordinary skill in the art. Nucleotide sequences of interest include, but are not limited to, coding sequences of structural genes (e.g., reporter genes, selection marker genes, oncogenes, drug resistance genes, growth factors, etc.), and non-coding regulatory sequences which do not encode an mRNA or protein product, (e.g., promoter sequence, polyadenylation sequence, termination sequence, enhancer sequence, etc.).

The term "susceptible" as used herein in reference to a cell describes the ability of a permissive or non-permissive host cell to adsorb and be penetrated by a virus. A cell line may be susceptible without being permissive in that it can be penetrated by a virus in the absence of viral proliferation and/or release of virions from the cell. A permissive cell line however must be susceptible. Susceptibility of a cell to a virus may be determined by methods known in the art such as detecting the presence of viral proteins using electrophoretic analysis (i.e., SDS-PAGE) of protein extracts prepared from the infected cell cultures.

The terms "permissive" and "permissiveness" as used herein describe the sequence of interactive events between a virus and its putative host cell. The process begins with viral adsorption to the host cell surface and ends with release of infectious virions. A cell is "permissive" (i.e., shows "permissiveness") if it is capable of supporting viral proliferation as determined by, for example, production of viral nucleic acid sequences and/or of viral peptide sequences, regardless of whether the viral nucleic acid sequences and viral peptide sequences are assembled into a virion. While not required, in a preferred embodiment, a cell is permissive if it generates virions and/or releases the virions contained therein. Many methods are available for the determination of the permissiveness of a given cell line. For example, the proliferation of a particular virus in a host cell line may be measured by the production of various viral markers including viral proteins, viral nucleic acid (including both RNA and DNA) and the progeny virus. The presence of viral proteins may be determined using electrophoretic analysis (i.e., SDS-PAGE) of protein extracts prepared from the infected cell cultures. Viral DNA or RNA may be quantitated using nucleic acid hybridization assays. Production of progeny virus may be determined by observation of a cytopathic effect. The invention is not limited to the specific quantity of proliferation of a virus.

The term "not permissive" means that the cell is not capable of supporting viral proliferation as determined by, for example, production of viral nucleic acid sequences and/or of viral peptide sequences, and/or assembly of viral nucleic acid sequences and viral peptide sequences into a virion.

The phrase "viral proliferation" as used herein describes the spread or passage of infectious virus from a permissive cell type to additional cells of either a permissive or susceptible character.

The terms "cytopathic effect" or "CPE" as used herein describe changes in cellular structure (i.e., a pathologic effect). Common cytopathic effects include cell destruction, syncytia (i.e., fused giant cells) formation, cell rounding, vacuole formation, and formation of inclusion bodies. CPE results from actions of a virus on permissive cells that negatively affect the ability of the permissive cellular host to preform its required functions to remain viable. In in vitro cell culture systems, CPE is evident when cells, as part of a confluent monolayer, show regions of nonconfluence after contact with a specimen that contains a virus. The observed microscopic effect is generally focal in nature and the foci are initiated by a single virion. However, depending upon viral load in the sample, CPE may be observed throughout the monolayer after a sufficient period of incubation. Cells demonstrating viral induced CPE usually change morphology to a rounded shape, and over a prolonged period of time can die and be released form their anchorage points in the monolayer. When many cells reach the point of focal destruction, the area is called a viral plaque, which appears as a hole in the monolayer. The terms "plaque" and "focus of viral infection" refer to a defined area of CPE which is usually the result of infection of the cell monolayer with a single infectious virus which then replicates and spreads to adjacent cells of the monolayer. Cytopathic effects are readily discernable and distinguishable by those skilled in the art.

As used herein the term "influenza virus" refers to members of the orthomyxoviridae family of enveloped viruses with a segmented antisense RNA genome (Knipe and Howley (eds.) *Fields Virology*, 4th edition, Lippincott Williams and Wilkins, Philadelphia, Pa. [2001]). Two types of influenza virus (A and B) are human pathogens causing respiratory pathology.

As used herein, the term "parainfluenza virus" refers to certain members of the paramyxoviridae genus of enveloped viruses with a single-stranded antisense RNA genome (Knipe and Howley (eds.) *Fields Virology*, 4th edition, Lippincott Williams and Wilkins, Philadelphia, Pa. [2001]). Four types of parainfluenza virus (1 to 4) are human respiratory pathogens.

DESCRIPTION OF THE INVENTION

The invention provides cell lines which are useful for the rapid detection and production of influenza and parainfluenza viruses. In particular, the invention relates to transgenic mink lung cells which show increased sensitivity to infection by influenza A, influenza B, or parainfluenza 3 viruses, or which are capable of enhanced productivity of infectious virions. The invention is suitable for use in culturing clinical influenza and parainfluenza virus isolates and for the production of influenza and parainfluenza virus for vaccine formulations, as antigen preparations for diagnostic applications, and for screening antiviral drugs.

The inventor contemplated that the mink lung cell proteases do not efficiently cleave-activate the hemagglutinin (HA) protein of influenza and the fusion (F) protein of parainfluenza viruses to generate the virulence factors HA1 and HA2, and F1 and F2, respectively. To correct this proposed deficiency, the human furin gene encoding an endoprotease which recognizes the consensus sequence R-X-K/R-R (located at the cleavage site of HA), was expressed in mink lung cells. Furin has been previously shown to play an important role in the cleavage of the HA protein of virulent avian influenza virus (Steineke-Grober et al., EMBO J. 11:2407–2414 [1992]; and Walker et al., J. Virol. 68:1213–1218 [1994]), the envelope glycoprotein of HIV (Morika et al., J. Virol. 67:3601–3604 [1993]; and Hallenberger et al., Nature 360:358–361 [1992]), the HA protein of measles virus (Watanbe et al., J. Virol. 69:3206–3210 [1995]), the glycoprotein of EBOLA virus (Volchkov et al., Proc. Natl. Acad. Sci. USA *95:5762–5767* [*1998*]), and the fusion (F) protein of parainfluenza virus 3 (Ortmann et al., J. Virol. 68:2772–2776 [1994]). Thus, the expression of human furin in mink lung cells was contemplated by the inventor, to greatly enhance the production of infectious influenza and parainfluenza viruses which require cleavage activation of a virulence factor possessing the furin consensus sequence. As can be seen in the following examples, transgenic mink lung cells expressing human furin possess increased sensitivity for the early detection of influenza A, influenza B and parainfluenza 3 viruses, and produce higher influenza A virus titers for suitable vaccine production and anti-viral drug screening applications.

More particularly, the invention provides transgenic mink lung epithelial cells (Mv1Lu) which express the human furin endoprotease (hF), as exemplified by the Mv1Lu-hF cell line. The increased sensitivity for the detection of influenza and parainfluenza viruses, makes the invention's transgenic mink lung epithelial cells a valuable tool for the rapid detection and/or isolation of influenza and parainfluenza viruses in clinical laboratories. In fact, the invention's transgenic mink lung epithelial cell lines allow detection of a broad spectrum of influenza and parainfluenza viruses within 1 to 2 days.

For example, data provided herein demonstrates that the exemplary Mv1Lu-hF cells of the invention have enhanced sensitivity to influenza and parainfluenza viruses as compared to Mv1Lu cells. In particular, compared to Mv1Lu cells, the invention's exemplary Mv1Lu-hF cells were more sensitive in detecting influenza A, influenza B and parainfluenza 3 viruses than were Mv1Lu cells (Examples 2, 4 and 5).

In addition to enhanced sensitivity to influenza and parainfluenza viruses, the invention's exemplary Mv1Lu-hF cells also produced a higher number of infectious influenza virions than did Mv1Lu cells. For example, data presented herein demonstrates that, the transgenic Mv1Lu-hF cells produced approximately 100-fold more infectious virus particles than did the parental Mv1Lu cells (Example 3).

The invention is further described under (A) Transgenic Mink Lung Cells Which Express Human Furin, (B) Cultures Containing Transgenic Mink Lung Cells, (C) Detection Of Influenza and Parainfluenza Viruses In Transgenic Mink Lung Cell Cultures, and (D) Production of High Titer Influenza and Parainfluenza Stocks in Transgenic Mink Lung Cell Cultures.

A. Transgenic Mink Lung Cells Which Express Human Furin

The invention provides transgenic mink lung epithelial cells (Mv1Lu) cells which express the human furin endoprotease (hF), as exemplified by the Mv1Lu-hF cell line. Furin is a subtilisin-like endopeptidase with substrate specificity for the consensus sequence R-X-K/R-R (SEQ ID NO:3) at the cleavage site (van de Ven et al., Mol. Biol. Rep., 14:265–75 [1990]). It was the inventors' consideration that the expression of human furin in a mink host cell would impart to the mink cell the ability to produce more infectious influenza and parainfluenza virions.

The invention's cells are exemplified by the transgenic mink lung epithelial cell line designated herein as Mv1Lu-hF. The term "transgenic cell line designated as Mv1Lu-hF" as used herein refers to any mink lung epithelial cell line expressing human furin. The cell line Mv1Lu-hF will be deposited at the American Type Culture Collection, 12301 Parklawn Drive, Rockville, Md. However, the invention is not limited to the transgenic cell line Mv1Lu-hF. Rather, the invention contemplates within its scope any transgenic mink ling epithelial cell line which expresses human furin.

For instance, the invention contemplates within its scope mink lung epithelial cells other than Mv1Lu cells, that have been transfected with human furin. Methods for isolation, culture and identification of epithelial lung cells from mink are known in the art. For example, Kniazeff et al. isolated in 1964 mink lung cells which gave rise to the exemplary Mv1Lu cells by trypsinization of lungs from nearly full-term, unsexed fetuses of the Aleutian mink (ATCC catalog number CCL-64, see "Comments"). A step-by-step description of trypsin-based isolation from fetal lungs and of cloning techniques are provided by Kniazeff et al., Lab. Invest. 5:495–500 [1976]. Other generic methods for isolation of epithelial lung cells are available in the art including, for example, collagenase treatment of lung tissue followed by selective trypsinization to remove residual fibroblasts (Milo et al., In Vitro, 20:899–911 [1984]), trypsin digestion of lung tissue followed by discontinuous Percoll gradient centrifugation (Richards et al., Lung 165:143–158 [1987]), and digestion of lung tissue with porcine pancreatic elastase followed by discontinuous metrizamide density gradient (Robinson et al., Am. Rev. Respir. Disease 130:1156–1160 [1984]).

The terms "transgenic" and "genetically engineered" when made in reference to a mink ling epithelial cell line refer to a mink ling epithelial cell line that contains a transgene which encodes human furin, or whose genome has been altered by the introduction of such a transgene by way of human intervention, such as by the methods described herein.

The terms "human furin," "human furin endoprotease," "human furin amino acid sequence," "human furin polypeptide," refer to the polypeptide sequence listed as SEQ ID NO:2 (FIG. 4, Panel B). It is also expressly contemplated that the term "human furin" includes variants of SEQ ID NO:2 which have the biological activity of SEQ ID NO:2.

A "variant" of SEQ ID NO:2 as used herein is defined as an amino acid sequence which differs by insertion, deletion, and/or conservative substitution of one or more amino acids from SEQ ID NO:2, respectively. The term "conservative substitution" of an amino acid refers to the replacement of that amino acid with another amino acid which has a similar hydrophobicity, polarity, and/or structure. For example, the following aliphatic amino acids with neutral side chains may be conservatively substituted one for the other: glycine, alanine, valine, leucine, isoleucine, serine, and threonine. Aromatic amino acids with neutral side chains which may be conservatively substituted one for the other include phenylalanine, tyrosine, and tryptophan. Cysteine and methionine are sulphur-containing amino acids which may be conservatively substituted one for the other. Also, asparagine may be conservatively substituted for glutamine, and vice versa, since both amino acids are amides of dicarboxylic amino acids. In addition, aspartic acid (aspartate) my be conservatively substituted for glutamic acid (glutamate) as both are acidic, charged (hydrophilic) amino acids. Also, lysine, arginine, and histidine may be conservatively substituted one for the other since each is a basic, charged (hydrophilic) amino acid. Guidance in determining which and how many amino acid residues may be substituted, inserted or deleted without abolishing biological or immunological activity may be found using computer programs well known in the art, for example, DNAStar software.

The term "has the biological activity SEQ ID NO:2" when made in reference to the biological activity of a variant of SEQ ID NO:2, refers to a quantity of substrate cleavage at the R-X-K/R-R (SEQ ID NO:3) consensus sequence which is greater than 1%, and more preferably from 2% to 500%, as compared to the quantity of substrate cleavage at the R-X-KIR-R (SEQ ID NO:3) consensus sequence of SEQ ID NO:2.

As used herein, the terms "nucleic acid molecule encoding," "DNA sequence encoding," and "DNA encoding" human furin and grammatical equivalents thereof, refer to the order or sequence of deoxyribonucleotides along a strand of deoxyribonucleic acid. The order of these deoxyribonucleotides determines the order of ribonucleotides along the mRNA chain, and also determines the order of amino acids along the polypeptide (protein) chain. The DNA sequence thus codes for the RNA sequence and for the amino acid sequence of human furin. In one preferred embodiment, the transgene comprises the nucleotide sequence (SEQ ID NO:1; FIG. 4, Panel A) which encodes the human furin endoprotease (SEQ ID NO:2; FIG. 4, Panel B).

While not required, in one embodiment, it may be desirable that the transgene further include a sequence encoding a selectable marker. The term "selectable marker" as used herein refers to nucleotide sequence which encodes an enzymatic activity that confers resistance to a compound (e.g., antibiotic or drug) upon the cell in which the selectable marker is expressed. Selectable markers may be "positive"; i.e., genes which encode an enzymatic activity which can be detected in any cell or cell line. Examples of dominant selectable markers include, but are not limited to, (1) the bacterial aminoglycoside 3' phosphotransferase gene (also referred to as the neo gene) which confers resistance to the drug G418 in cells, (2) the bacterial hygromycin G phosphotransferase (hyg) gene which confers resistance to the antibiotic hygromycin, and (3) the bacterial xanthine-guanine phosphoribosyl transferase gene (also referred to as the gpt gene) which confers the ability to grow in the presence of mycophenolic acid. Other selectable markers are not dominant in that their use must be in conjunction with a cell line that lacks the relevant enzyme activity. Selectable markers may be "negative"; negative selectable markers encode an enzymatic activity whose expression is cytotoxic to the cell when grown in an appropriate selective medium. For example, the HSV-tk gene and the dt gene are commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme. Similarly, the expression of the dt gene selects against cells capable of expressing the Diphtheria toxin. In one preferred embodiment, the selectable marker gene used is the neo gene in plasmid pcDNA3 (Invitrogen). As described in Example 1, cells which incorporated this transgene were selected by exposure to Geneticin (G418) (Gibco-BRL Inc.).

Vectors (e.g., plasmids, linear DNA, viruses, etc.) which contain a nucleotide sequence that encodes the human decay accelerating factor may be introduced into cells using techniques well known in the art. The term "introducing" a nucleic acid sequence into a cell refers to the introduction of the nucleic acid sequence into a target cell to produce a transformed cell. Methods of introducing nucleic acid sequences into cells are well known in the art. For example, where the nucleic acid sequence is a plasmid or naked piece of linear DNA, the sequence may be "transfected" into the cell using, for example, calcium phosphate-DNA co-precipitation, DEAE-dextran-mediated transfection, polybrene-mediated transfection, electroporation, microinjection, liposome fusion, lipofection, protoplast fusion, and biolistics. Alternatively, where the nucleic acid sequence is encapsidated into a viral particle, the sequence may be introduced into a cell by "infecting" the cell with the virus. In a preferred embodiment, the vector is a plasmid.

Transformation of a cell may be stable or transient. The terms "transient transformation" and "transiently transformed" refer to the introduction of one or more nucleotide sequences of interest into a cell in the absence of integration of the nucleotide sequence of interest into the host cell's genome. Transient transformation may be detected by, for example, enzyme-linked immunosorbent assay (ELISA) which detects the presence of a polypeptide encoded by one or more of the nucleotide sequences of interest. Alternatively, transient transformation may be detected by detecting the activity of the protein (e.g., β-glucuronidase) encoded by the nucleotide sequence of interest. The term "transient transformant" refer to a cell which has transiently incorporated one or more nucleotide sequences of interest.

In contrast, the terms "stable transformation" and "stably transformed" refer to the introduction and integration of one or more nucleotide sequence of interest into the genome of a cell. Thus, a "stable transformant" is distinguished from a transient transformant in that, whereas genomic DNA from the stable transformant contains one or more nucleotide sequences of interest, genomic DNA from the transient transformant does not contain the nucleotide sequence of interest. Stable transformation of a cell may be detected by Southern blot hybridization of genomic DNA of the transformed cell using nucleic acid sequences which are capable of binding to the nucleotide sequence of interest. Alternatively, stable transformation of a cell may also be detected by the polymerase chain reaction of genomic DNA of the transformed cell to amplify the nucleotide sequence of interest. In a preferred embodiment, transformation is stable as demonstrated by expression of human furin by the exemplary transgenic cell line Mv1Lu-hF after multiple passages (Example 1 and FIG. 1).

In one preferred embodiment, the transgenic Mv1Lu-hF cells provided herein express human furin. The term "express human furin" when made in reference to a cell means that the cell contains a detectable quantity of human furin. Expression of the human furin protein may be determined directly or indirectly using methods known in the art. For example, indirect detection may be achieved by immunofluorescence assays such as those disclosed herein, wherein the transfected cells are incubated with an anti-human furin monoclonal antibody (Alexis Biochemicals) and FITC-conjugated goat anti-mouse IgG as a second antibody, followed by observation of immunofluorescence under the microscope.

Alternatively, expression of the human furin may be determined indirectly by detecting the activity of a reporter protein which is encoded by a reporter gene (e.g., the uid A gene) that is operably linked to the gene which encodes the human furin protein. The term "reporter gene" refers to a gene which encodes a reporter molecule (e.g., RNA, polypeptide, etc.) which is detectable in any detection system, including, but not limited to enzyme (e.g., ELISA, as well as enzyme-based histochemical assays), fluorescent, radioactive, and luminescent systems. Exemplary reporter genes include, for example, β-glucuronidase gene, green fluorescent protein gene, E. coli β-galactosidase gene, human placental alkaline phosphatase gene, and chloramphenicol acetyltransferase gene. It is not intended that the present invention be limited to any particular detection system or label.

In a preferred embodiment, the number of transformed Mv1Lu cells which express human furin may be enriched relative to Mv1Lu cells which do not express human furin by using methods known in the art, such as those disclosed herein. For example, cells may be labeled with anti-human furin monoclonal antibody and FITC conjugated goat anti-mouse IgG (Chemicon), to monitor fusin expression. Cell clones expressing fusin may then be obtained by limiting dilution.

While the invention is illustrated using the exemplary transgenic Mv1Lu-hF cells deposited on Oct. 2, 2002 at the American Type Culture Collection, 10801 University Blvd., Manassas, Va. 20110-2209, as ATCC number PTA-4737, it is expressly contemplated that the invention is not limited to this particular cell type. Rather, the invention contemplates within its scope any cell line which is established from the transgenic cell line designated herein as Mv1Lu-hF cells.

The term "established from" when made in reference to a cell line in relation to the transgenic cell line designated Mv1Lu-hF deposited on Oct. 2, 2002 at the American Type Culture Collection, 10801 University Blvd., Manassas, Va. 20110–2209, as ATCC number PTA-4737, refers to a cell line which has been obtained (e.g., isolated, purified, etc.) from the transgenic cell line designated Mv1Lu-hF, using any manipulation, such as, without limitation, infection with virus, transfection with DNA sequences, treatment and/or mutagenesis using for example chemicals, radiation, etc., selection of any cell that is contained in the transgenic cell line designated Mv1Lu-hF, etc. For example, a cell line established from the transgenic cell line designated Mv1Lu-hF includes Mv1Lu-hF cells which have been treated with chemical compounds [e.g., N-ethyl-N-nitrosurea (ENU), methylnitrosourea (MNU), procarbazine hydrochloride (PRC), triethylene melamine (TEM), acrylamide monomer (AA), chlorambucil (CHL), melphalan (MLP), cyclophosphamide (CPP), diethyl sulfate (DES), ethyl methane sulfonate (EMS), methyl methane sulfonate (MMS), 6-mercaptopurine (6MP), mitomycin-C (MMC), procarbazine (PRC), N-methyl-N'-nitro-N-nitrosoguanidine (MNNG), $^3H_2O$, and urethane (UR)], and electromagnetic radiation [e.g., X-ray radiation, gamma-radiation, ultraviolet light].

Data provided herein also demonstrate that the exemplary transgenic Mv1Lu-hF cells of the invention show increased sensitivity for infection by influenza A, influenza B and parainfluenza 3 viruses as compared to Mv1Lu cells from which the invention's transgenic cells were derived. The term "sensitivity" and "sensitive" when made in reference to a cell is a relative term which refers to the degree of permissiveness of the cell to a virus as compared to the degree of permissiveness of another cell to the same virus.

For example, the terms "increased sensitivity to influenza" and "increased sensitivity to parainfluenza" when used in reference to the invention's transgenic Mv1Lu-hF cell lines refers to an increase of least 2 fold, more preferably 2 fold to 10 fold, yet more preferably 10 to 100 fold, and most preferably greater than 100 fold, in the quantity of infected transgenic mink lung cells as compared to the control Mv1Lu cells. For example, if 24 infected Mv1Lu cells and 115 transgenic mink lung cells were observed in inoculated cultures, than the increase in sensitivity would be over 4 fold.

The cells of the invention are also characterized by "enhanced productivity of infectious virions." As used herein this phrase refers to the production of preferably at least 2 fold, more preferably 2 fold to 10 fold, yet more preferably 10 to 100 fold, and most preferably greater than 100 fold more infectious influenza A, influenza B or parainfluenza 3 virus particles by the transgenic mink lung cell line, as compared to the control Mv1Lu cell line. For example, if $10^5$ infectious virions per ml were obtained from the Mv1Lu cell line and $10^7$ infectious virions per ml were obtained from the transgenic mink lung cell, than the enhancement in productivity would be 100 fold.

B. Cultures Containing Transgenic Mink Lung Cells

The invention provides single-cell type cultures of transgenic mink lung cells for detecting the presence of influenza and parainfluenza viruses. The term "single-cell type culture" refers to a composition, whether liquid, gel, or solid, which contains a single type of cell. Data presented herein demonstrates that the exemplary Mv1Lu-hF cell line was more sensitive to influenza A, influenza B and parainfluenza 3 virus infection than was the parental Mv1Lu cell line.

The invention further provides mixed-cell type cultures which contain a cell type other than the transgenic mink lung cells of the invention in combination with the invention's transgenic mink lung cells. These mixed-cell type cultures are useful for detecting the presence of respiratory viruses such as influenza A, influenza B and parainfluenza 3.

As used herein, the term "mixed-cell type culture" refers to a composition, whether liquid, gel, or solid, which contains a mixture of two or more types of cells wherein the cell types are mingled together. For example, a mixed-cell type culture may contain cells from different tissues or organs from the same species and same genus. Alternatively, a mixed-cell type culture may contain cells from different species in the same genus. Yet another alternative is that a mixed-cell type culture contain cells from a different genus. The present invention encompasses any combination of cell types suitable for the detection, identification, and/or quantitation of viruses in samples, including mixed cell cultures in which all of the cell types used are not genetically engineered, mixtures in which one or more of the cell types are genetically engineered and the remaining cell types are not genetically engineered, and mixtures in which all of the cell types are genetically engineered.

The term "cell type different from the transgenic mink lung cell line" as used herein means any cell type which differs in any way from the transgenic mink cell line. This term includes, without limitation, the parental Mv1Lu cell line; any cell type which is established from a cell type other than the parental Mv1Lu cell line; and any cell type established from the Mv1Lu-hF cell line. In particular, the term "cell type different from the transgenic mink lung epithelial cell line" expressly includes Mv1Lu cells which either have not been transfected with the hF gene, or which have been transfected with a transgene containing one or more nucleotide sequences of interest. Further, the term "cell type different from the transgenic mink lung epithelial cell line" expressly includes Mv1Lu-hF cells deposited on Oct. 2, 2002 at the American Type Culture Collection, 10801 University Blvd., Manassas, Va. 20110-2209, as ATCC number PTA-4737, and which have additionally been transfected with a transgene containing one or more nucleotide sequences of interest. which have additionally been transfected with a transgene containing one or more nucleotide sequences of interest.

An advantage of using the invention's transgenic Mv1Lu-hF cells in mixed-cell-type culture is that such cultures provide rapid and sensitive assay systems in a single mixed-cell type unit that is both suitable for diagnostic assays as well as eliminates the need for multiple cell lines cultured in individual containers.

While not limiting the invention to any particular cell type, exemplary cell lines which may be used in mixed-cell type cultures with the invention's transgenic Mv1Lu-hF cells and which can detect respiratory viruses such as influenza and parainfluenza, are listed in Table 1.

TABLE 1

Exemplary Cell Lines For Mixed-Cell Type Cultures With The Invention's Mv1Lu-hF Cell Line

| Cell Line | ATCC No. | Source | Virus[a] |
|---|---|---|---|
| primary monkey | none[b] | Kidney, rhesus monkey | Herpes, entero, adeno, myxo, paramy |
| BS-C-1 | CCL26 | Kidney, African green monkey | Herpes, entero, adeno, myxo, paramy |
| CV-1 | CCL70 | Kidney, African green monkey | Herpes, entero, adeno, myxo, paramy |
| Vero | CCL81 | Kidney, African green monkey | Herpes, entero, adeno, myxo, paramy |
| Vero 76 | CRL1587 | Kidney, African green monkey | Herpes, entero, adeno, myxo, paramy |
| Vero C1008 | CRL1586 | Kidney, African green monkey | Herpes, entero, adeno, myxo, paramy |
| Vero 76 | CCL81 | Kidney, African green monkey | Herpes, entero, adeno, myxo, paramy |
| Cos-1 | CRL1650 | Kidney, African green monkey, transformed | Herpes, entero, adeno, myxo, paramy |
| Cos-7 | CRL1651 | Kidney, African green monkey, transformed | Herpes, entero, adeno, myxo, paramy |
| FRhK-4 | CRL1688 | Kidney, fetal rhesus monkey | Herpes, entero, adeno, myxo, paramy |
| LLC-MK2 original | CCL7 | Kidney, rhesus monkey | Herpes, entero, adeno, myxo, paramy |
| LLC-MK2 derivative | CCL7.1 | Kidney, rhesus monkey | Herpes, entero, adeno, myxo, paramy |
| MDCK | CCL34 | Kidney, canine | Herpes, entero, adeno, myxo, paramy |
| CCD-13 Lu | CCL200 | Lung, human | Herpes, entero, adeno, paramy |
| CCD-8 Lu | CCL201 | Lung, human | Herpes, entero, adeno, paramy |
| CCD-14 Br | CCL203 | Bronchiole, human | Herpes, entero, adeno, myxo, paramy |
| CCD-16 Lu | CCL204 | Lung, human | Herpes, entero, adeno, paramy |
| CCD-18 Lu | CCL205 | Lung, human | Herpes, entero, adeno, paramy |
| CCD-19 Lu | CCL210 | Lung, human | Herpes, entero, adeno, paramy |
| Hs888 Lu | CCL211 | Lung, human | Herpes, entero, adeno, paramy |
| MRC-9 | CCL212 | Lung, human | Herpes, entero, adeno, paramy |
| CCD-25 Lu | CCL215 | Lung, human | Herpes, entero, adeno, paramy |
| WiDr | CCL218 | Colon, adenocarcinoma, human | Herpes, entero, adeno |
| DLD-1 | CCL221 | Colon, adenocarcinoma, human | Herpes, entero, adeno |
| COLO205 | CCL222 | Colon, adenocarcinoma, human | Herpes, entero, adeno |
| HCT-15 | CCL222 | Colon, adenocarcinoma, human | Herpes, entero, adeno |

TABLE 1-continued

Exemplary Cell Lines For Mixed-Cell Type Cultures
With The Invention's Mv1Lu-hF Cell Line

| Cell Line | ATCC No. | Source | Virus[a] |
|---|---|---|---|
| SW 480 | CCL228 | Colon, adenocarcinoma, human | Herpes, entero, adeno |
| LOVO | CCL229 | Colon, adenocarcinoma, human | Herpes, entero, adeno |
| SW403 | CCL230 | Colon, adenocarcinoma, human | Herpes, entero, adeno |
| SW48 | CCL231 | Colon, adenocarcinoma, human | Herpes, entero, adeno |
| SW116 | CCL233 | Colon, adenocarcinoma, human | Herpes, entero, adeno |
| SW1463 | CCL234 | Colon, adenocarcinoma, human | Herpes, entero, adeno |
| SW837 | CCL235 | Rectum, adenocarcinoma, human | Herpes, entero, adeno |
| SW948 | CCL237 | Colon, adenocarcinoma, human | Herpes, entero, adeno |
| SW1417 | CCL238 | Colon, adenocarcinoma, human | Herpes, entero, adeno |
| FHs74 Int | CCL241 | Small intestine, adenocarcinoma, human | Herpes, entero, adeno |
| HCT-8 | CCL244 | Adenocarcinoma, ileococal | Herpes, entero, adeno |
| HCT-116 | CCL247 | Colon carcinoma, human | Herpes, entero, adeno |
| T84 | CCL248 | Colon carcinoma, human | Herpes, entero, adeno |
| NCI-H747 | CCL252 | Cecum, adenocarcinoma, human | Herpes, entero, adeno |
| NCI-H508 | CCL253 | Cecum, adenocarcinoma, human | Herpes, entero, adeno |
| LS123 | CCL255 | Colon, human, adenocarcinoma | Herpes, entero, adeno |
| CaCo-2 | HTB37 | Colon, adenocarcinoma, human | Herpes, entero, adeno |
| HT-29 | HTB38 | Colon, adenocarcinoma, human | Herpes, entero, adeno |
| SK-CO-1 | HTB39 | Colon, adenocarcinoma, human | Herpes, entero, adeno |
| HuTu 80 | HTB40 | Duodenum, adenocarcinoma, human | Herpes, entero, adeno |
| A253 | HTB41 | Epidemoid carcinoma | Herpes, entero, adeno, paramyo |
| A704 | HTB45 | Kidney adenocarcinoma, human | Herpes, entero, adeno, paramyo |
| Hela | CCL2 | Epitheloid carcinoma, cervix, human | Herpes, entero, adeno, myxo, paramy |
| Hela | CCL2.1 | Epitheloid carcinoma, cervix, human | Herpes, entero, adeno, myxo, paramy |
| Hela53 | CCL2.2 | Epitheloid carcinoma, cervix, human | Herpes, entero, adeno, myxo, paramy |
| L-132 | CCL5 | Embryonic lung, human, Hela marker | Herpes, entero, adeno, myxo, paramy |
| Intestine | CCL6 | Embryonic intestine, human, Hela marker | Herpes, entero, adeno |
| BHK-21 | CCL10 | Kidney, synister or golden hamster | Herpes, entero, adeno, myxo, paramy |
| Hak | CCL15 | Kidney, syn hamster | Herpes, entero, adeno, myxo, paramy |
| KB | CCL17 | Epidermoid carcinoma oral, human | Herpes, entero, adeno, paramy |
| Hep-2 | CCL23 | Epidermoid carcinoma larynx, human | Herpes, entero, adeno, paramy |
| Wish | CCL25 | Ammion, human | Herpes, entero, adeno |
| Detroit 532 | CCL54 | Skin, human | Herpes, entero, adeno |
| FL | CCL62 | Ammion, human | Herpes, entero |
| Detroit 525 | CCL65 | Skin, human | Herpes, entero, adeno |
| Detroit 529 | CCL66 | Skin, human | Herpes, entero, adeno |
| Detroit 510 | CCL72 | Skin, human | Herpes, entero, adeno |
| WI-38 | CCL75 | Lung, diploid human | Herpes, entero, adeno, paramy |
| WI-38 VA13 | CCL75.1 | Lung, diploid human, SV-40 transformed | Herpes, entero, adeno, paramy |
| Citrullinemia | CCL76 | Skin, human | Herpes, entero, adeno, paramy |
| Spik (NBL-10) | CCL78 | Kidney, dolphin | Herpes, entero, adeno |
| Detroit 539 | CCL84 | Skin, human | Herpes, entero, adeno |
| Cridu Chat | CCL90 | Skin, human | Herpes, entero, adeno |
| WI26 VA4 | CCL95.1 | Lung, human | Herpes, entero, adeno, paramy |
| BeWo | CCL98 | Choriocarcinoma, human | Herpes, entero, adeno |
| SW-13 | CCL105 | Adenocarcinoma, human, adrenal cortex | Herpes, entero, adeno |
| Detroit 548 | CCL116 | Skin | Herpes, entero, adeno |
| Detroit 573 | CCL117 | Skin | Herpes, entero, adeno |
| HT-1080 | CCL121 | Fibrocarcinoma, human | Herpes, entero, adeno |
| HG 261 | CCL122 | Skin, human | Herpes, entero, adeno |
| C211 | CCL123 | Skin, human | Herpes, entero, adeno |
| Amdur II | CCL124 | Skin, human | Herpes, entero, adeno |
| CHP 3 (M. W.) | CCL132 | Skin, human, fibroid like | Herpes, entero, adeno |
| CHP 4 (W. W.) | CCL133 | Skin, human, fibroid like | Herpes, entero, adeno |
| RD | CCL136 | Rhabdomyosarcoma | Herpes, entero, adeno |
| HEL 299 | CCL137 | Lung, diploid | Herpes, entero, adeno, paramy |

TABLE 1-continued

Exemplary Cell Lines For Mixed-Cell Type Cultures
With The Invention's Mv1Lu-hF Cell Line

| Cell Line | ATCC No. | Source | Virus[a] |
|---|---|---|---|
| Detroit 562 | CCL138 | Carcinoma, pharynx | Herpes, entero, adeno, myxo, paramy |
| MRC-5 | CCL171 | Lung, diploid, human | Herpes, entero, adeno, paramy |
| A-549 | CCL185 | Lung, carcinoma, human | Herpes, entero, adeno, myxo, paramy |
| IMR-90 | CCL186 | Lung, carcinoma, human | Herpes, entero, adeno, myxo, paramy |
| LS180 | CCL187 | Colon, adenocarcinoma, human | Herpes, entero, adeno |
| LS174T | CCL188 | Colon, adenocarcinoma, human | Herpes, entero, adeno |

[a]Herpes = Herpes viruses Entero = Enteroviruses Adeno = Adenoviruses Myxo = Myxoviruses Paramy = Paramyxoviruses
[b]Primary monkey kidney cells may be obtained from Diagnostic Hybrids (catalog numbers 490102A for shell format and 49-0600A for tube format)

Methods for preparing mixed-cell type cultures are known in the art, such as those disclosed in U.S. Pat. No. 5,939,253 issued on Aug. 17, 1999 to Scholl et al., and U.S. Pat. No. 6,168,915 issued on Jan. 2, 2001 to Scholl et al., the entire contents of which are herein incorporated by reference. Briefly, cell line monolayers are cultured to confluence. The terms "confluence" and "confluent" as used herein in reference to an adherent cell line define a condition wherein cells throughout a culture are in contact with each other creating what appears to be a continuous sheet or "monolayer" of cells. The cell monolayers are rinsed with Hank's Balanced Salt Solution (HBSS) without magnesium or calcium. Depending upon the cell line, the cells may be dissociated by adding trypsin (0.125% in HBSS, without calcium or magnesium) or trypsin-EDTA (0.25% in 1 mM EDTA in HBSS, without calcium or magnesium) directly to the cell monolayer, and incubating for approximately 5 minutes at ambient temperature. Cell culture medium is added to each trypsinized cell suspension and the cells are repeatedly pipetted in order to produce near-single cell suspensions (i.e., without cell aggregates). Each trypsinized cell suspension is diluted in an adequate volume of culture medium to produce an optical density of cell suspension suitable to produce a confluent monolayer of cells within 2–3 days of incubation in a 96-well microtiter plate.

Mixed-cell type monolayers may be produced by co-plating two different cell types at an equal volume of each diluted cell suspension (e.g, 0.1 ml of each cell type is used to inoculate each well of a 96-well microtiter plate). The cells are allowed to attach to the well surface by gravity for 30–60 minutes, and the inoculated microtiter plates are incubated for up to three days at 36° C. in 5% $CO_2$ with 95% relative humidity.

Periodically during incubation, the mixed-cell type monolayers are checked for overall viability and for the ability of the cell lines to co-exist and develop as a single cell sheet (i.e., a single monolayer), with two different cell morphologies (i.e., dimorphic cell sheets), at an approximately equal density of each cell type. At confluence, the cells may be treated with a methylene blue staining solution to fix the cells and stain them a light blue in order to provide contrast for visualization using light microscopy.

Mixed-cell type cultures preferably contain a mixed cell monolayer adhered to the well surfaces. The adhered monolayer cultures may exhibit a smooth, evenly distributed monolayer, with each cell type being easily distinguished and surviving in a mixed-cell type monolayer, giving the appearance of a single cell distribution. Alternatively, the adhered monolayer cultures may exhibit two different morphologies at confluence, in which separate, different patches of each cell line co-exist within the monolayer, giving the appearance of oil mixing with water.

C. Detection of Influenza and Parainfluenza Viruses In Transgenic Mink Lung Cell Cultures Following the incubation of the single-cell type or mixed-cell type monolayers, the monolayers are inoculated with specimens suspected of containing an influenza or a parainfluenza virus or with a stock viral culture (i.e., a positive control). Negative or uninfected control cultures may also be employed; these cultures receive culture medium lacking any influenza or parainfluenza virus. To inoculate a culture, an aliquot of the specimen to be tested is placed in a suitable standard culture medium in standard culture vessels.

Inoculation may be performed using any method suitable for the type of culture employed (i.e., plate, shell vial or tube culture). When plate cultures or shell vials are employed, solutions suspected of containing influenza or parainfluenza (or known control solutions) are dispensed into the wells of the plates and the shell vials may be centrifuged for about 1 hour at 700 g at room temperature. When tube cultures are employed this centrifugation step is not required. Following "inoculation" (i.e., exposure of the monolayer to a specimen containing or suspected of containing infectious virus), the monolayers are incubated at 37° C. for a sufficient period of time (e.g., from about 3 hours to about 5 days) for the virus infectious cycle to proceed. The presence of influenza or parainfluenza in the specimen may be detected by, for example, by observing hemadsorption or immunofluorescence, as described in Examples 2–5.

D. Production of High Titer Influenza and Parainfluenza Stocks In Transgenic Mink Lung Cell Cultures To prepare inactivated influenza vaccines, virus produced from Mv1Lu-hF cells is isolated from the culture medium by affinity chromatography using cellufine sulphate (Palache et al., J. Infect. Dis. 176(suppl. 1):S20–S23 [1997]). The intact live virus is inactivated after purification by any one of a number of methods known in the art, such as formalin or propiolactone treatment to produce an inactivated viral vaccine. Specifically, influenza virus is inactivated by incubation of the virus suspension in 0.1% formadelhyde for 10 to 14 days at 4° C. The inactivated viral preparation is then tested in mice using standard protocols, before use in human clinical trials.

Additionally, the virus produced by Mv1Lu-hF cells is contemplated to be useful in antigen preparations for enzyme linked immunosorbent assays. For instance, the virus is suitable for diagnostic applications for detection of viral antibodies in patient serum when used as an antigen to coat the wells of microtiter plates (or in antigen capture assays). The virus is also useful as a positive control antigen in testing virus from clinical specimens.

Equally important, the virus production of the transgenic Mv1Lu-hF cells render it an excellent cell line for use in various anti-viral drug screening applications. For instance, candidate antiviral drugs are incubated with the influenza-infected Mv1Lu-hF cells. Comparison of the influenza virus titers produced by the treated cells with the titers produced by untreated cells provides a mechanism for determining whether the candidate drug has anti-viral activity in vitro.

EXPERIMENTAL

The following examples serve to illustrate certain preferred embodiments and aspects of the present invention and are not to be construed as limiting the scope thereof.

In the experimental disclosure which follows, the following abbreviations apply: M (Molar); µM (micromolar); N (Normal); mol (moles); mmol (millimoles); µmol (micromoles); nmol (nanomoles); g (grams); mg (milligrams); µg (micrograms); ng (nanograms); 1 or L (liters); ml (milliliters); µl (microliters); cm (centimeters); mm (millimeters); µm (micrometers); nm (nanometers); xg (times gravity); ° C. (degrees Centigrade); FBS (fetal bovine serum); PBS (phosphate buffered saline; HEPES (N-[2-hydroxyethyl]piperazine-N'-[2-ethanesulfonic acid]); HBSS (Hank's Balanced Salt Solution); MEM (Minimal Essential Medium); EMEM (Eagle's Minimal Essential Medium); RBCs (red blood cells); HAD (hemadsorption); BBL (Becton Dickinson Microbiology Systems, Cockeysville, Md.); DIFCO (Difco Laboratories, Detroit, Mich.); U.S. Biochemical (U.S. Biochemical Corp., Cleveland, Ohio); Chemicon (Chemicon International, Inc., Temecula, Calif.); Dako (Dako Corporation, Carpinteria, Calif.); Fisher (Fisher Scientific, Pittsburgh, Pa.); Sigma (Sigma Chemical Co., St. Louis, Mo.); ATCC (American Type Culture Collection, Rockville, Md.); Bartel's (Bartels, Issaquah, Wash.); and BioWhittaker (BioWhittaker, Warrensville, Md.); Charles River (Charles River Laboratories, Wilmington, Mass.); Clinical Research Institute (Clinical Research Institute of Montreal, Montreal CANADA) Diagnostic Hybrids (Diagnostic Hybrids, Inc., Athens, Ohio); Invitrogen (Invitrogen Corporation, Carlsbad, Calif.); Qiagen (Qiagen Inc., Valencia, Calif.) Gene Therapy Systems (Gene Therapy Systems, Inc., San Diego, Calif.) and Alexis (Alexis Biochemicals Inc., San Diego, Calif.).

EXAMPLE 1

Generation of Transgenic Mink Lung (Mv1Lu) Cells Which Express Human Furin (hF)

Monolayers of mink lung cells (ATCC #CCL-64) were subcultured after treatment with trypsin, seeded into wells of 12-well plates in the presence of E-MEM culture medium (Diagnostic Hybrids), and incubated at 36° C. incubator for 48 hr. The freshly formed cell monolayer was subsequently used for transfection.

The human furin gene (GenBank Accession Number X17094; and FIG. 4, Panel A) was cloned in pcDNA3 using standard molecular biological techniques. The pcDNA3 plasmid which is commercially available from Invitrogen, is a standard eukaryotic expression vector with a cytomegalovirus enhancer/promoter flanking the multiple cloning site, and containing a neomycin-resistance cassette permitting the selection for stable transfectants. The plasmid DNA of pcDNA3-hF obtained from Dr. Nabil G. Seidah (Clinical Research Institute) was used to transform $E.$ $coli$, and bacterial colonies which contained the plasmid DNA were selected and expanded by growing in broth culture for 18 hr. The plasmid DNA was purified from the bacteria using a commercial kit (Qiagen) and was used to transfect Mv1Lu cells by using GenePORTER2™ (Gene Therapy Systems) as a carrier, following the manufacturers instructions to generate Mv1Lu-hF cells.

Transfected cells were incubated for another two days and Geneticin (G418) (Gibco-BRL) was added to select stable transfectants. After 6 days, most of the cells died and the surviving cells began to grow. Once the viable cells formed a monolayer, they were subcultured. A portion of the cells was used to test for human furin expression by staining with an anti-human furin convertase monoclonal antibody (Alexis) as a primary antibody and fluorescein (FITC) conjugated goat anti-mouse IgG (Chemicon) as a secondary antibody. About 10% of the geneticin-selected cells expressed furin.

In order to enrich cells expressing human furin, the geneticin-selected cells were removed by trypsinization, and cloned by limiting dilution. After 2 weeks in culture, the cloned cells had formed a monolayer. An aliquot of cells from each clone was subsequently removed and assessed for furin expression as described above. Approximately 50% of the cells from several of the clones expressed human furin. One of these was selected for another round of cloning by limiting dilution. After 2 weeks in culture, the cloned cells had formed a monolayer. Human furin expression by the new clones was assessed again by staining with the anti-human furin monoclonal antibody. One clone with 100% of the cells expressing human furin was selected for further analysis. This clone, Mv1Lu-hF, was expanded by serial subculture. As demonstrated by immunofluorescence, human furin expression was maintained (See, FIG. 1). The Mv1Lu-hF cells were deposited on Oct. 2, 2002 at the American Type Culture Collection, 10801 University Blvd., Manassas, Va. 20110-2209, as ATCC number PTA-4737.

EXAMPLE 2

Detection of Influenza A Virus From Clinical Samples Using Mv1Lu-hF Cells

Figure 2:
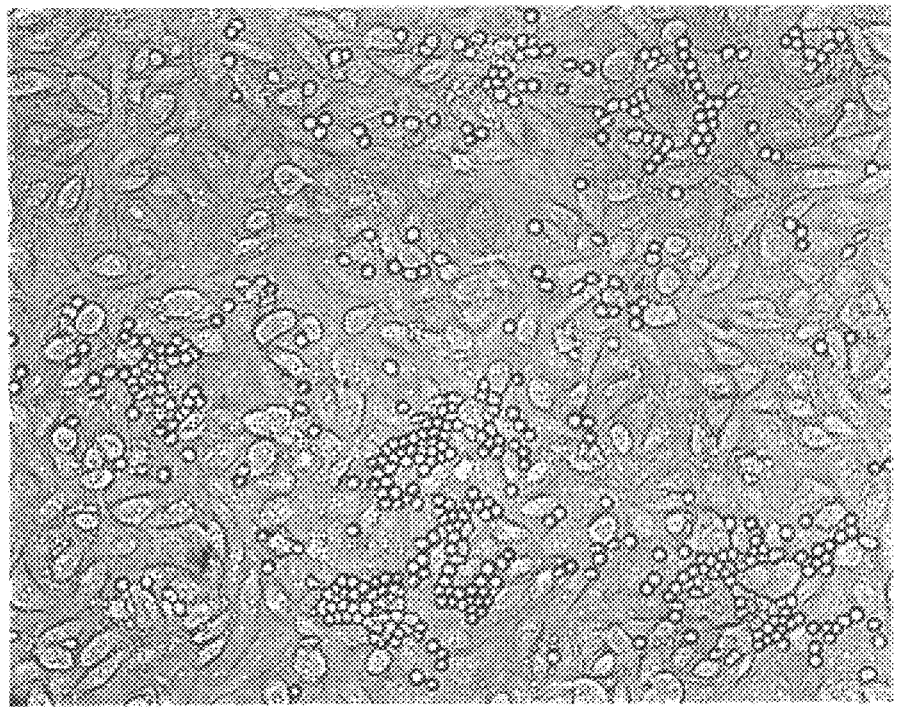
FIG. 2 depicts hemadsorption of guinea pig red blood cells by (A) Mv1Lu cells infected with influenza A, and (B) transgenic Mv1Lu-hF cells infected with influenza A.
Figure 2:
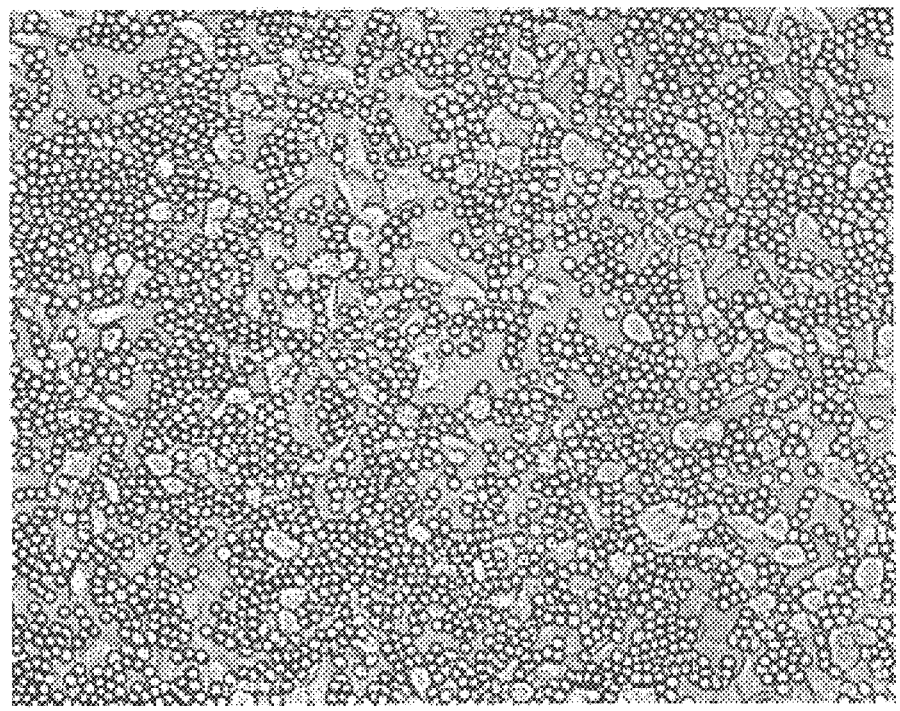

To compare the sensitivity for the detection of Influenza A by Mv1Lu-hF cells with the parental Mv1Lu cells, the hemadsorption (HAD) and immunofluorescence staining of infected cells was determined as follows. Briefly, each cell type was seeded at a density of $2\times10^5$ cells/ml onto a 48-well plate using 0.2 ml per well. After the cells formed a monolayer (usually about 2–3 days), 17 previously tested influenza A virus-positive clinical samples from frozen stocks were inoculated into two wells of each cell with an inoculum of 5 µL/well. After overnight incubation at 36° C. in a 5% $CO_2$ atmosphere, the medium was removed and 0.2 ml of guinea pig red blood cells (RBC) was added. The guinea pig RBCs collected in heparin (Charles River) were washed three times in phosphate buffered saline (PBS) and then resuspended at a concentration of 0.2% of RBC, prior to use. After incubating the plates at 4° C. for 30 min, the loose RBCs were removed by shaking and aspiration. The RBCs adsorbed to the influenza A virus-infected cells appeared in clumps, as shown in FIG. 2.

Figure 3:
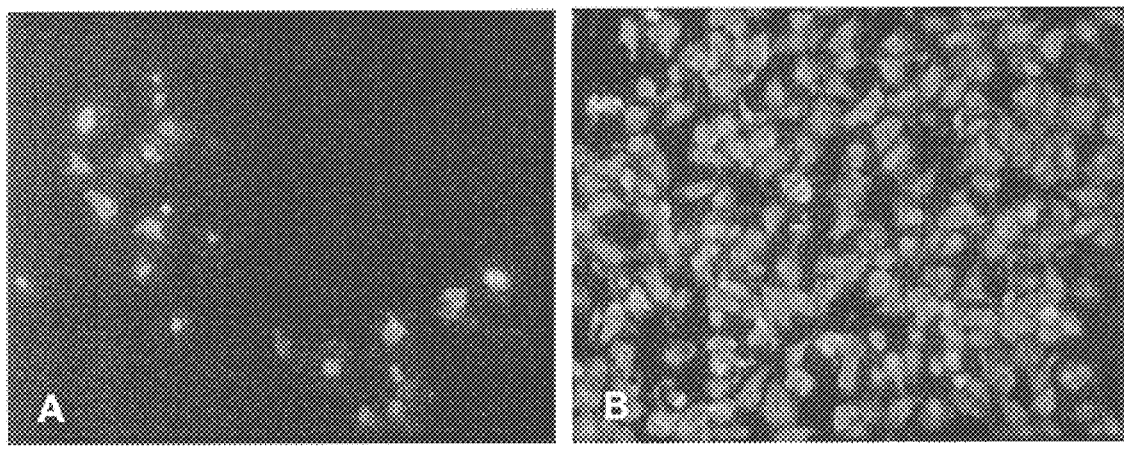
FIG. 3 shows immunofluorescence staining of influenza A by (A) Mv1Lu cells infected with influenza A, and (B) transgenic Mv1Lu-hF cells infected with influenza A.

The HAD test is a method used to determine whether an inoculated culture is infected with virus from a clinical specimen. The plates from the HAD test described above were examined under an inverted microscope and the results were duly recorded. The RBCs attached to the influenza A-infected cells were lysed with 0.2 ml water for 10 seconds. The cells were then fixed with 80% acetone for 1 to 5 min. After removing the fixative, the cells were stained with a FITC-conjugated anti-influenza A virus monoclonal antibody (Diagnostic Hybrids) for 30 min in the dark. The cells were then washed twice with PBS and examined under a fluorescence microscope. The detection of fluorescent cells (apple green in appearance) indicates that the cells were infected with influenza A, with greater numbers of fluorescent cells indicative of increased infectivity. As shown in FIG. 3, the transgenic Mv1Lu-hF cells were more sensitive to human influenza A virus infection than were the parental Mv1Lu cells. The results obtained for all 17 clinical isolates are listed in Table 2, as the proportion of cells in the well which show hemadsorption upon visual examination. In particular, the following nomenclature was used to express hemadsorption as a percentage of cells:—means 0%, 1+ means from about 1% to about 25%, 2+ means from about 25% to about 50%, 3+ means from about 50% to about 75%, and 4+ means from about 75% to about 100%.

By hemadsorption, the use of the parental Mv1Lu cells permitted the detection of 12 positives by day 1 postinfection and 8 positives by day 3 postinfection. The inability to detect 5 specimens on day 3 that had been previously detected on day 1, indicates that the newly produced progeny virions were not as infectious as the virions in the clinical specimen. The only exception was the virus in specimen #1 which was undetectable on day 1 and detectable on day 3. In contrast, the transgenic Mv1Lu-hF cells permitted the detection of 15 positives by day 1 postinfection and all 17 positives by day 3 postinfection. As shown in both FIG. 2 and Table 1, more RBCs were adsorbed to the transgenic Mv1Lu-Hf cells than to the parental Mv1Lu cells in most of the samples. Importantly, the high detection rate and high hemadsorption proportion indicates that the influenza A virions produced by the transgenic Mv1Lu-hF cells were highly infectious. Taken together, these results indicate that the Mv1Lu-hF cells are more sensitive for early detection and produce more virus for later detection, than the parental Mv1Lu cells.

TABLE 2

Comparison Of Mv1Lu to Mv1Lu-hF For Detection Of Influenza A By Hemadsorption

| Specimen | Day | Mv1Lu | Mv1Lu-hF |
|---|---|---|---|
| 1 | 1 | — | 1+ |
|   | 3 | 1+ | 3+ |
| 2 | 1 | 1+ | 3+ |
|   | 3 | 1+ | 4+ |
| 3 | 1 | 1+ | 2+ |
|   | 3 | 1+ | 3+ |
| 4 | 1 | 1+ | 1+ |
|   | 3 | — | 3+ |
| 5 | 1 | 1+ | 2+ |
|   | 3 | 1+ | 4+ |
| 6 | 1 | 1+ | 2+ |
|   | 3 | — | 4+ |
| 7 | 1 | 2+ | 3+ |
|   | 3 | — | 4+ |
| 8 | 1 | 1+ | 1+ |
|   | 3 | 1+ | 4+ |
| 9 | 1 | — | 1+ |
|   | 3 | — | 4+ |
| 10 | 1 | — | — |
|    | 3 | — | 4+ |
| 11 | 1 | 1+ | 1+ |
|    | 3 | 1+ | 4+ |
| 12 | 1 | — | 1+ |
|    | 3 | — | 2+ |
| 13 | 1 | 1+ | 1+ |
|    | 3 | 1+ | 3+ |
| 14 | 1 | 1+ | 1+ |
|    | 3 | 1+ | 4+ |
| 15 | 1 | 2+ | 1+ |
|    | 3 | — | 4+ |
| 16 | 1 | 1+ | 2+ |
|    | 3 | — | 4+ |
| 17 | 1 | — | — |
|    | 3 | — | 4+ |

TABLE 3

Comparison Of Mv1Lu to Mv1Lu-hF For Detection Of Influenza A By Immunofluorescence

| Specimen | Day | Mv1Lu | Mv1Lu-hF |
|---|---|---|---|
| 1 | 1 | <1 | 1+ |
|   | 3 | <1 | 3+ |
| 2 | 1 | <1 | 2+ |
|   | 3 | 1+ | 4+ |
| 3 | 1 | 1+ | 2+ |
|   | 3 | <1 | 4+ |
| 4 | 1 | 1+ | 2+ |
|   | 3 | <1 | 4+ |
| 5 | 1 | 1+ | 3+ |
|   | 3 | <1 | 4+ |
| 6 | 1 | 1+ | 4+ |
|   | 3 | <1 | 4+ |
| 7 | 1 | <1 | 3+ |
|   | 3 | <1 | 4+ |
| 8 | 1 | <1 | <1 |
|   | 3 | — | 4+ |
| 9 | 1 | <1 | 2+ |
|   | 3 | <1 | 4+ |
| 10 | 1 | 1+ | 2+ |
|    | 3 | <1 | 4+ |
| 11 | 1 | 1+ | 3+ |
|    | 3 | <1 | 4+ |
| 12 | 1 | <1 | <1 |
|    | 3 | — | 1+ |
| 13 | 1 | <1 | 1+ |
|    | 3 | — | 3+ |
| 14 | 1 | 1+ | 2+ |
|    | 3 | <1 | 4+ |
| 15 | 1 | 2+ | 4+ |
|    | 3 | <1 | 4+ |
| 16 | 1 | 2+ | 2+ |
|    | 3 | <1 | 4+ |
| 17 | 1 | <1 | <1 |
|    | 3 | — | 3+ |

The results from this experiment are also listed in Table 3, as the proportion of cells in the well which show immunofluorescence upon visual examination. In particular, the following nomenclature was used to express immunofluorescence as a stained cell percentage:—means 0%, <1 means greater than 0% to about 1%, 1+ means from about 1% to about 25%, 2+ means from about 25% to about 50%, 3+ means from about 50% to about 75%, and 4+ means from about 75% to about 100%. By immunofluorescence, the use of the parental Mv1Lu cells permitted the detection of all 17 positives by day 1 postinfection, but by day 3, 4 of these were negative and the majority had fewer numbers of stained cells. In contrast, on day 1 greater numbers of stained cells were found in wells containing the transgenic Mv1Lu-hF cells (except in #8), and by day 3 the number of stained cells had increased over that observed on day 1. Thus, immunofluorescence is a more sensitive assay of infection than is hemadsorption with guinea pig RBCs. Additionally, by both immunofluorescence and hemadsorption, the transgenic Mv1Lu-hF cells provide a more sensitive detection system for clinical isolates of influenza A virus, than does the parental cell line.

EXAMPLE 3

Production of Influenza A Virus Using Mv1Lu-hF Cells

Mink lung epithelial cells are an alternative to Madin-Darby canine kidney (MDCK) epithelial cells for the isolation and cultivation of human influenza viruses (See, Schultz-Cherry et al., J. Clin. Microbiol. 36:3718–3720 [1998]; and Huang and Turchek, J. Clin. Microbiol. 38:422–423 [2000]). The results obtained during the development of the present invention and shown in Example 2 above, indicate that mink lung cells expressing human furin (Mv1Lu-hF) are suitable for the production of high titer influenza A virus stocks for vaccine preparations.

TABLE 4

Comparison of Influenza A Virus Titers

| Virus | H1N1 | | H3N2 | |
|---|---|---|---|---|
| Cells | Mv1Lu | Mv1Lu-hF | Mv1Lu | Mv1Lu-HF |
| Day 1 | $2.5 \times 10^4$ | $1.0 \times 10^5$ | $5.0 \times 10^4$ | $5.0 \times 10^4$ |
| Day 2 | $1.5 \times 10^5$ | $1.0 \times 10^7$ | $5.0 \times 10^5$ | $4.0 \times 10^6$ |
| Day 3 | $1.0 \times 10^5$ | $2.0 \times 10^7$ | $2.5 \times 10^4$ | $5.0 \times 10^7$ |

The transgenic Mv1Lu-hF and parental Mv1Lu cells were plated in 24 well plates and inoculated at a multiplicity of infection of 0.01 with two subtypes of influenza A virus as described in Example 2. The influenza A virus isolates chosen for this experiment included an H1N1 isolate (ATCC #VR-95) and an H3N2 isolate (ATCC #VR-822). Supernatants were collected at multiple time points postinfection and were used to enumerate virus titer by inoculating shell vials of R-Mix cells (Diagnostic Hybrids) with 10-fold serial dilutions. After incubation of the shell vials overnight at 37° C., the cell monolayers were stained with an influenza A-virus specific antibody and examined by fluorescence microscopy (See, Example 2). The positive cells from each well were counted and these numbers were used to determine viral titers. As shown in Table 4, the transgenic Mv1Lu-hF cells produced 100 fold more infectious virions than the parental Mv1Lu cells. Thus, Mv1Lu-hF cells are a superior cell line for the production of influenza A vaccines as demonstrated by the exemplary H1N1 and H3N2 virus isolates.

EXAMPLE 4

Detection of Influenza B Virus From Clinical Samples Using Mv1Lu-hF Cells

To compare the sensitivity for the detection of influenza B virus by the transgenic Mv1Lu-hF cells with the parental Mv1Lu cells, 4 frozen clinical specimens that had previously tested positive, were used to inoculate both cells cultured in 24-well plates. After incubation overnight at 36° C., the cells were stained with an anti-influenza B virus antibody (Diagnostic Hybrids) and the positive fluorescent stained cells were counted.

TABLE 5

Comparison of Influenza B Virus Infectivity

| Influenza B Isolate | #s of Infected Mv1Lu Cells | #s of Infected Mv1Lu-hF cells |
|---|---|---|
| 1 | 24 | 115 |
| 2 | 55 | 231 |
| 3 | 16 | 82 |
| 4 | 4 | 15 |

As shown in Table 5, the transgenic Mv1Lu-hF cells were about 4–5 times more sensitive than the parental Mv1Lu-hF cells for rapid detection of influenza B virus. In a related experiment, both cells were incubated for three days over infection before stained with the anti-influenza B virus antibody. After this longer incubation period, no positive cells were detected in wells of the parental Mv1Lu cells, while many positive cells were detected in wells of the transgenic Mv1Lu-Hf cells. This indicates that the influenza B virus progeny produced by the transgenic Mv1Lu-hF cells, but not the parental Mv1Lu cells, were infectious.

EXAMPLE 5

Detection of Parainfluenza Virus 3 from Clinical Samples Using Mv1Lu-hF Cells To compare the sensitivity for the detection of parainfluenza virus by the transgenic Mv1Lu-hF cells with the parental Mv1Lu cells, 5 frozen clinical specimens that had previously tested positive, were used to inoculate both cells cultured in 24-well plates. After incubation for 40 hr at 36° C., the cells were stained with an anti-parainfluenza virus 3 antibody (Diagnostic Hybrids) and the positive fluorescent stained cells were counted.

TABLE 6

Comparison of Parainfluenza Virus 3 Infectivity

| Parainfluenza 3 Isolate | #s of Infected Mv1Lu Cells | #s of Infected My1Lu-hF cells |
|---|---|---|
| 1 | 124 | 213 |
| 2 | 251 | 459 |
| 3 | 24 | 72 |
| 4 | 63 | 183 |
| 5 | 12 | 45 |

As shown in Table 6, the transgenic Mv1Lu-hF cells were about 2–3 times more sensitive than the parental Mv1Lu-hF cells for rapid detection of parainfluenza virus 3. Thus, the transgenic Mv1Lu-hF cells offer improved sensitivity for the detection of parainfluenza virus 3 from clinical specimens.

From the above, it is clear that the invention provides cells which have enhanced sensitivity for influenza A, influenza B and parainfluenza 3 and which are useful for the rapid detection of influenza and parainfluenza viruses from clinical specimens. Additionally, the invention provides cells which are useful for the production of high titers of infectious influenza and parainfluenza viruses for inclusion in vaccines and/or diagnostic compositions.

All publications and patents mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art and in fields related thereto are intended to be within the scope of the following claims.

What is claimed is:

1. A transgenic mink lung epithelial cell line expressing human furin, wherein said cell line has a property selected from the group consisting of (a) increased sensitivity to at least one virus selected from the group consisting of influenza A virus, influenza B virus and parainfluenza virus 3, as compared to Mv1Lu, and (b) enhanced productivity of infectious virions upon inoculation with at least one virus selected from the group one consisting of influenza A virus, influenza B virus and parainfluenza virus 3, as compared to Mv1Lu.

2. The cell line of claim 1, wherein said human furin is encoded by the sequence SEQ ID NO:1.

3. The cell line of claim 1, wherein said transgenic mink lung epithelial cell line has the sensitivity of the cell line designated Mv1Lu-hF and deposited as ATCC number PTA-4737, to at least one virus selected from the group consisting of influenza A virus, influenza B virus and parainfluenza virus 3.

4. A transgenic cell line designated Mv1Lu-hF and deposited as ATCC number PTA-4737.

5. A cell line established from a transgenic cell line designated Mv1Lu-hF and deposited as ATCC number PTA-4737, wherein said established cell line has a property selected from the group consisting of (a) increased sensitivity to at least one virus selected from the group consisting of influenza A virus, influenza B virus and parainfluenza virus 3, as compared to the Mv1Lu cell line, and (b) enhanced productivity of infectious virions upon inoculation with at least one virus selected from the group one consisting of influenza A virus, influenza B virus and parainfluenza virus 3, as compared to the Mv1Lu cell line.

6. The cell line of claim 5, wherein said cell line has the sensitivity of the cell line designated Mv1Lu-hF and deposited as ATCC number PTA-4737, to at least one virus selected from the group consisting of influenza A virus, influenza B virus and parainfluenza virus 3.

7. A composition comprising a transgenic mink lung epithelial cell expressing human furin, wherein said cell has a property selected from the group consisting of (a) increased sensitivity to at least one virus selected from the group consisting of influenza A virus, influenza B virus and parainfluenza virus 3, as compared to the Mv1Lu cell line, and (b) enhanced productivity of infectious virions upon inoculation with at least one virus selected from the group one consisting of influenza A virus, influenza B virus and parainfluenza virus 3, as compared to the Mv1Lu cell line.

8. The composition of claim 7, wherein said composition further comprises a second cell type different from said transgenic mink lung epithelial cell, and wherein said transgenic mink lung epithelial cell and said second cell type are in mixed-cell type culture.

9. A composition comprising a transgenic cell designated Mv1Lu-hF and deposited as ATCC number PTA-4737.

10. The composition of claim 9, wherein said composition further comprises a second cell type different from said Mv1Lu-hF cell, and wherein said Mv1Lu-hF cell and said second cell type are in mixed-cell type culture.

11. A composition comprising a cell established from a transgenic cell line designated Mv1Lu-hF and deposited as ATCC number PTA-4737, wherein said established cell has a property selected from the group consisting of (a) increased sensitivity to at least one virus selected from the group consisting of influenza A virus, influenza B virus and parainfluenza virus 3, as compared to the Mv1Lu cell line, and (b) enhanced productivity of infectious virions upon inoculation with at least one virus selected from the group one consisting of influenza A virus, influenza B virus and parainfluenza virus 3, as compared to the Mv1Lu cell line.

12. The composition of claim 11, wherein said composition further comprises a second cell type different from said established cell, and wherein said established cell and said second cell type are in mixed-cell type culture.

13. A method for detection of a virus selected from the group consisting of influenza A virus, influenza B virus and parainfluenza virus 3, in a sample, comprising:
  a) providing:
    i) a sample suspected of containing said virus; and
    ii) a composition comprising a cell designated Mv1Lu-hF and deposited as ATCC number PTA-4737;
  b) inoculating said cell with said sample to produce an inoculated cell; and
  c) observing said inoculated cell for the presence of said virus.

14. The method of claim 13, wherein said composition further comprises a second cell type different from said Mv1Lu-hF cell, and wherein said Mv1Lu-hF cell and said second cell type are in mixed-cell type culture.

15. The method of claim 13, further comprising, providing a monoclonal antibody selected from the group consisting of an influenza A virus-reactive monoclonal antibody, an influenza B virus-reactive monoclonal antibody, and a parainfluenza virus 3-reactive monoclonal antibody, and wherein step c) comprises using said monoclonal antibody for observation of said virus.

16. A kit for detection of a virus selected from the group consisting of influenza A virus, influenza B virus and parainfluenza virus 3, in a sample, comprising:
  a) a composition comprising a cell designated Mv1Lu-hF and deposited as ATCC number PTA-4737; and
  b) a monoclonal antibody selected from the group consisting of an influenza A virus-reactive monoclonal antibody, an influenza B virus-reactive monoclonal antibody, and a parainfluenza virus 3-reactive monoclonal antibody.

17. The kit of claim 16, wherein said composition further comprises a second cell type different from said Mv1Lu-hF cell, and wherein said Mv1Lu-hF cell and said second cell type are in mixed-cell type culture.

18. A method for producing virus selected from the group consisting of influenza A virus, influenza B virus and parainfluenza virus 3, comprising:
  a) providing:
    i) a sample containing said virus, and
    ii) a composition comprising a cell designated Mv1Lu-hF and deposited as ATCC number PTA-4737; and
  b) inoculating said cell with said sample to produce an inoculated cell, wherein said cell produces said virus.

* * * * *

SEQUENCE LISTING

<160> NUMBER OF SEQ ID NOS: 3

<210> SEQ ID NO 1
<211> LENGTH: 2388
<212> TYPE: DNA
<213> ORGANISM: Homo sapiens

<400> SEQUENCE: 1

| | | | | | |
|---|---|---|---|---|---|
| atggagctga | ggccctggtt | gctatgggtg | gtagcagcaa | caggaacctt | ggtcctgcta | 60 |
| gcagctgatg | ctcagggcca | gaaggtcttc | accaacacgt | gggctgtgcg | catccctgga | 120 |
| ggcccagcgg | tggccaacag | tgtggcacgg | aagcatgggt | tcctcaacct | gggccagatc | 180 |
| ttcgggact | attaccactt | ctggcatcga | ggagtgacga | agcggtccct | gtcgcctcac | 240 |
| cgcccgcggc | acagccggct | gcagagggag | cctcaagtac | agtggctgga | acagcaggtg | 300 |
| gcaaagcgac | ggactaaacg | ggacgtgtac | caggagccca | cagaccccaa | gtttcctcag | 360 |
| cagtggtacc | tgtctggtgt | cactcagcgg | gacctgaatg | tgaaggcggc | ctgggcgcag | 420 |
| ggctacacag | ggcacggcat | tgtggtctcc | attctggacg | atggcatcga | gaagaaccac | 480 |
| ccggacttgg | caggcaatta | tgatcctggg | gccagttttg | atgtcaatga | ccaggaccct | 540 |
| gaccccagc | ctcggtacac | acagatgaat | gacaacaggc | acgtcacacg | gtgtgcgggg | 600 |
| gaagtggctg | cggtggccaa | caacggtgtc | tgtggtgtag | gtgtggccta | caacgcccgc | 660 |
| attggagggg | tgcgcatgct | ggatggcgag | gtgacagatg | cagtggaggc | acgctcgctg | 720 |
| ggcctgaacc | ccaaccacat | ccacatctac | agtgccagct | ggggccccga | ggatgacggc | 780 |
| aagacagtgg | atgggccagc | ccgcctcgcc | gaggaggcct | tcttccgtgg | ggttagccag | 840 |
| ggccgagggg | ggctgggctc | catctttgtc | tgggcctcgg | ggaacggggg | ccgggaacat | 900 |
| gacagctgca | actgcgacgg | ctacaccaac | agtatctaca | cgctgtccat | cagcagcgcc | 960 |
| acgcagtttg | gcaacgtgcc | gtggtacagc | gaggcctgct | cgtccacact | ggccacgacc | 1020 |
| tacagcagtg | gcaaccagaa | tgagaagcag | atcgtgacga | ctgacttgcg | gcagaagtgc | 1080 |
| acggagtctc | acacgggcac | ctcagcctct | gcccccttag | cagccggcat | cattgctctc | 1140 |
| accctggagg | ccaataagaa | cctcacatgg | cgggacatgc | aacacctggt | ggtacagacc | 1200 |
| tcgaagccag | cccacctcaa | tgccaacgac | tgggccacca | atggtgtggg | ccggaaagtg | 1260 |
| agccactcat | atggctacgg | gcttttggac | gcaggcgcca | tggtggccct | ggcccagaat | 1320 |
| tggaccacag | tggcccccca | gcggaagtgc | atcatcgaca | tcctcaccga | gcccaaagac | 1380 |
| atcgggaaac | ggctcgaggt | gcggaagacc | gtgaccgcgt | gcctgggcga | gcccaaccac | 1440 |
| atcactcggc | tggagcacgc | tcaggcgcgg | ctcacccctgt | cctataatcg | ccgtggcgac | 1500 |
| ctggccatcc | acctggtcag | ccccatgggc | acccgctcca | ccctgctggc | agccaggcca | 1560 |
| catgactact | ccgcagatgg | gtttaatgac | tgggccttca | tgacaactca | ttcctgggat | 1620 |
| gaggatccct | ctggcgagtg | ggtcctagag | attgaaaaca | ccagcgaagc | caacaactat | 1680 |
| gggacgctga | ccaagttcac | cctcgtactc | tatggcaccg | ccctgagggg | gctgcccgta | 1740 |
| cctccagaaa | gcagtggctg | caagaccctc | acgtccagtc | aggcctgtgt | ggtgtgcgag | 1800 |

-continued

```
gaaggcttct ccctgcacca gaagagctgt gtccagcact gccctccagg cttcgccccc    1860
caagtcctcg atacgcacta tagcaccgag aatgacgtgg agaccatccg ggccagcgtc    1920 tgcgcccct gccacgcctc atgtgccaca tgccaggggc cggccctgac agactgcctc    1980
agctgcccca gccacgcctc cttggaccct gtggagcaga cttgctcccg gcaaagccag    2040
agcagccgag agtccccgcc acagcagcag ccacctcggc tgcccccgga ggtggaggcg    2100
gggcaacggc tgcgggcagg gctgctgccc tcacacctgc ctgaggtggt ggccggcctc    2160
agctgcgcct tcatcgtgct ggtcttcgtc actgtcttcc tggtcctgca gctgcgctct    2220
ggctttagtt ttcgggggg t gaaggtgtac accatggacc gtggcctcat ctcctacaag    2280
gggctgcccc ctgaagcctg gcaggaggag tgcccgtctg actcagaaga ggacgagggc    2340
cggggcgaga ggaccgcctt tatcaaagac cagagcgccc tctgatga               2388
```

<210> SEQ ID NO 2
<211> LENGTH: 794
<212> TYPE: PRT
<213> ORGANISM: Homo sapiens

<400> SEQUENCE: 2

```
Met Glu Leu Arg Pro Trp Leu Leu Trp Val Val Ala Ala Thr Gly Thr
1               5                   10                  15

Leu Val Leu Leu Ala Ala Asp Ala Gln Gly Gln Lys Val Phe Thr Asn
            20                  25                  30

Thr Trp Ala Val Arg Ile Pro Gly Gly Pro Ala Val Ala Asn Ser Val
        35                  40                  45

Ala Arg Lys His Gly Phe Leu Asn Leu Gly Gln Ile Phe Gly Asp Tyr
    50                  55                  60

Tyr His Phe Trp His Arg Gly Val Thr Lys Arg Ser Leu Ser Pro His
65                  70                  75                  80

Arg Pro Arg His Ser Arg Leu Gln Arg Glu Pro Gln Val Gln Trp Leu
                85                  90                  95

Glu Gln Gln Val Ala Lys Arg Arg Thr Lys Arg Asp Val Tyr Gln Glu
            100                 105                 110

Pro Thr Asp Pro Lys Phe Pro Gln Gln Trp Tyr Leu Ser Gly Val Thr
        115                 120                 125

Gln Arg Asp Leu Asn Val Lys Ala Ala Trp Ala Gln Gly Tyr Thr Gly
    130                 135                 140

His Gly Ile Val Val Ser Ile Leu Asp Asp Gly Ile Glu Lys Asn His
145                 150                 155                 160

Pro Asp Leu Ala Gly Asn Tyr Asp Pro Gly Ala Ser Phe Asp Val Asn
                165                 170                 175

Asp Gln Asp Pro Asp Pro Gln Pro Arg Tyr Thr Gln Met Asn Asp Asn
            180                 185                 190

Arg His Gly Thr Arg Cys Ala Gly Glu Val Ala Ala Val Ala Asn Asn
        195                 200                 205

Gly Val Cys Gly Val Gly Val Ala Tyr Asn Ala Arg Ile Gly Gly Val
    210                 215                 220

Arg Met Leu Asp Gly Glu Val Thr Asp Ala Val Glu Ala Arg Ser Leu
225                 230                 235                 240

Gly Leu Asn Pro Asn His Ile His Ile Tyr Ser Ala Ser Trp Gly Pro
                245                 250                 255

Glu Asp Asp Gly Lys Thr Val Asp Gly Pro Ala Arg Leu Ala Glu Glu
            260                 265                 270
```

-continued

```
Ala Phe Phe Arg Gly Val Ser Gln Gly Arg Gly Leu Gly Ser Ile
            275                 280                 285

Phe Val Trp Ala Ser Gly Asn Gly Arg Glu His Asp Ser Cys Asn
        290                 295                 300

Cys Asp Gly Tyr Thr Asn Ser Ile Tyr Thr Leu Ser Ile Ser Ser Ala
305                 310                 315                 320

Thr Gln Phe Gly Asn Val Pro Trp Tyr Ser Glu Ala Cys Ser Ser Thr
                325                 330                 335

Leu Ala Thr Thr Tyr Ser Ser Gly Asn Gln Asn Glu Lys Gln Ile Val
            340                 345                 350

Thr Thr Asp Leu Arg Gln Lys Cys Thr Glu Ser His Thr Gly Thr Ser
        355                 360                 365

Ala Ser Ala Pro Leu Ala Ala Gly Ile Ile Ala Leu Thr Leu Glu Ala
    370                 375                 380

Asn Lys Asn Leu Thr Trp Arg Asp Met Gln His Leu Val Val Gln Thr
385                 390                 395                 400

Ser Lys Pro Ala His Leu Asn Ala Asn Asp Trp Ala Thr Asn Gly Val
                405                 410                 415

Gly Arg Lys Val Ser His Ser Tyr Gly Tyr Gly Leu Leu Asp Ala Gly
            420                 425                 430

Ala Met Val Ala Leu Ala Gln Asn Trp Thr Thr Val Ala Pro Gln Arg
        435                 440                 445

Lys Cys Ile Ile Asp Ile Leu Thr Glu Pro Lys Asp Ile Gly Lys Arg
    450                 455                 460

Leu Glu Val Arg Lys Thr Val Thr Ala Cys Leu Gly Glu Pro Asn His
465                 470                 475                 480

Ile Thr Arg Leu Glu His Ala Gln Ala Arg Leu Thr Leu Ser Tyr Asn
                485                 490                 495

Arg Arg Gly Asp Leu Ala Ile His Leu Val Ser Pro Met Gly Thr Arg
            500                 505                 510

Ser Thr Leu Leu Ala Ala Arg Pro His Asp Tyr Ser Ala Asp Gly Phe
        515                 520                 525

Asn Asp Trp Ala Phe Met Thr Thr His Ser Trp Asp Glu Asp Pro Ser
530                 535                 540

Gly Glu Trp Val Leu Glu Ile Glu Asn Thr Ser Glu Ala Asn Asn Tyr
545                 550                 555                 560

Gly Thr Leu Thr Lys Phe Thr Leu Val Leu Tyr Gly Thr Ala Pro Glu
                565                 570                 575

Gly Leu Pro Val Pro Pro Glu Ser Ser Gly Cys Lys Thr Leu Thr Ser
            580                 585                 590

Ser Gln Ala Cys Val Val Cys Glu Glu Gly Phe Ser Leu His Gln Lys
        595                 600                 605

Ser Cys Val Gln His Cys Pro Pro Gly Phe Ala Pro Gln Val Leu Asp
    610                 615                 620

Thr His Tyr Ser Thr Glu Asn Asp Val Glu Thr Ile Arg Ala Ser Val
625                 630                 635                 640

Cys Ala Pro Cys His Ala Ser Cys Ala Thr Cys Gln Gly Pro Ala Leu
                645                 650                 655

Thr Asp Cys Leu Ser Cys Pro Ser His Ala Ser Leu Asp Pro Val Glu
            660                 665                 670

Gln Thr Cys Ser Arg Gln Ser Gln Ser Ser Arg Glu Ser Pro Pro Gln
        675                 680                 685

Gln Gln Pro Pro Arg Leu Pro Pro Glu Val Glu Ala Gly Gln Arg Leu
```

```
                690                 695                 700
Arg Ala Gly Leu Leu Pro Ser His Leu Pro Glu Val Val Ala Gly Leu
705                 710                 715                 720

Ser Cys Ala Phe Ile Val Leu Val Phe Val Thr Val Phe Leu Val Leu
                725                 730                 735

Gln Leu Arg Ser Gly Phe Ser Phe Arg Gly Val Lys Val Tyr Thr Met
            740                 745                 750

Asp Arg Gly Leu Ile Ser Tyr Lys Gly Leu Pro Pro Glu Ala Trp Gln
        755                 760                 765

Glu Glu Cys Pro Ser Asp Ser Glu Glu Asp Glu Gly Arg Gly Glu Arg
    770                 775                 780

Thr Ala Phe Ile Lys Asp Gln Ser Ala Leu
785                 790

<210> SEQ ID NO 3
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: The residue at this position can be any amino
      acid.
<220> FEATURE:
<221> NAME/KEY: MISC_FEATURE
<222> LOCATION: (3)..(3)
<223> OTHER INFORMATION: The residue at this position can be Lys or Arg.

<400> SEQUENCE: 3

Arg Xaa Xaa Arg
1
```